(12) United States Patent
Stone et al.

(10) Patent No.: US 6,218,534 B1
(45) Date of Patent: Apr. 17, 2001

(54) PREPARATION OF ASYMMETRIC CYCLIC UREAS THROUGH A MONOACYLATED DIAMINE INTERMEDIATE

(75) Inventors: Benjamin R. P. Stone; Luigi Anzalone, both of West Chester, PA (US); Joseph M. Fortunak, Newark, DE (US); Gregory D. Harris, Wilmington, DE (US); Ioannis I. Valvis, Hockessin, DE (US); Robert E. Waltermire, Wilmington, DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/166,507

(22) Filed: Oct. 5, 1998

Related U.S. Application Data
(60) Provisional application No. 60/061,195, filed on Oct. 6, 1997.

(51) Int. Cl.[7] ................... C07D 403/10; C07D 401/056
(52) U.S. Cl. ................... 540/492; 540/495; 540/503
(58) Field of Search .................. 540/503, 492, 540/495

(56) References Cited

U.S. PATENT DOCUMENTS

| | | | |
|---|---|---|---|
| 5,530,124 | 6/1996 | Radesca et al. | 540/503 |
| 5,532,356 | 7/1996 | Smyser et al. | 540/492 |
| 5,532,357 | 7/1996 | Rodgers et al. | 540/492 |
| 5,610,294 | 3/1997 | Lam et al. | 540/492 |
| 5,998,614 | * 12/1999 | Smyser | 540/492 |

OTHER PUBLICATIONS

Shawe et al., Regiospecific Monoprotection of N–Methyl-ethylenediamine, *Synthetic Communications*, 26(19), pp. 3633–3636 (1996).

Blacklock et al., Synthesis of Semisynthetic Dipeptides Using N–Carboxyanhydrides and Chiral Induction on Raney Nickel. A Method of Practical for Large Scale, *J. Org. Chem.*, 53, pp. 836–844 (1988).

Leclerc et al., On the Selectivity of Acylation of Unprotected Diamino Acids, *Canadian Journal of Chemistry*, vol. 46, pp. 1047–1051 (1968).

Xu et al., Ethyl Trifluoroacetate: A Powerful Reagent for Differentiating Amino Groups, *Tetrahedron Letters*, vol. 36, No. 41, pp. 7367–7360 (1995).

Fokin et al., The Fluoroacylation of Diamines, *Izv. Akad. Nauk. sssr. Ser. Khim*, 1981, pp. 863–866.

* cited by examiner

Primary Examiner—Mukund J. Shah
Assistant Examiner—Thomas McKenzie

(57) ABSTRACT

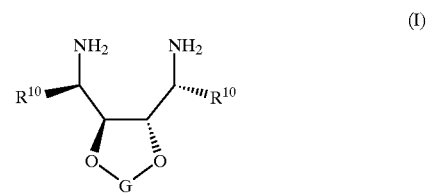

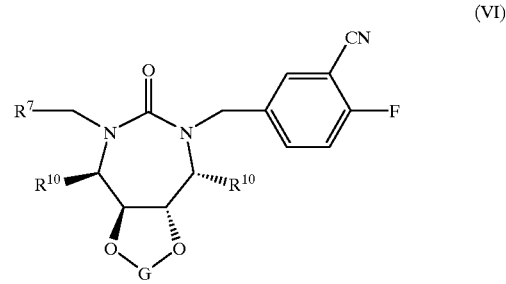

A process for the preparation of asymmetric cyclic ureas of Formula (VI) starting from the diamine of Formula (I). In the process, a compound of Formual (I), wherein G is a group selected from —C(—CH$_2$CH$_2$CH$_2$CH$_2$CH$_2$—)—, —C(CH$_2$CH$_3$)$_2$—, —C(CH$_3$)(CH$_2$CH$_3$)—, —C(CH$_2$CH$_2$CH$_2$CH$_3$)$_2$—, —C(CH$_3$)(CH$_2$CH(CH$_3$)CH$_3$)—, —CH(phenyl)—, —CH$_2$—, —C(CH$_3$)$_2$—, and —C(OCH$_3$)(CH$_2$CH$_2$CH$_3$)—, is selectively monoacylated with an acylating agent to give an asymmetric monoacylated diamine, 2) the asymmetric monoacylated diamine is contacted with an aldehyde and a reducing agent to form a monoalkylated monoacylated diamine, 3) the monoalkylated monoacylated diamine is contacted with a strong base to form a monoalkylated de-acylated diamine, 4) the monoalkylated de-acylated diamine is contacted with 3-cyano-4-fluoro-benzaldehyde and a reducing agent to form a dialkylated diamine, and 5) the dialkylated diamine is contacted with phosgene in the presence of a base to form a compound of Formula (VI). The invention allows for scalable preparation of a wide variety of asymmetrical cyclic ureas useful as HIV protease inhibitors for the treatment of HIV infection.

28 Claims, No Drawings

PREPARATION OF ASYMMETRIC CYCLIC UREAS THROUGH A MONOACYLATED DIAMINE INTERMEDIATE

This application claims the benefit of U.S. Provisional Application No. 60/061,195, filed Oct. 6, 1997.

FIELD OF THE INVENTION

The present invention describes a method for the preparation of asymmetric N,N'-disubstituted cyclic ureas, which are useful as HIV protease inhibitors, through the selective acylation of substituted 1,4 diamino butanes.

BACKGROUND OF THE INVENTION

U.S. Pat. No. 5,610,294 discloses cyclic urea compounds of formula (X) which are useful as HIV protease inhibitor compounds.

(X)

U.S. Pat. No. 5,532,357 discloses methods for the preparation of compounds of formula (X), for example compound (X-a) via the isourea intermediate (XX).

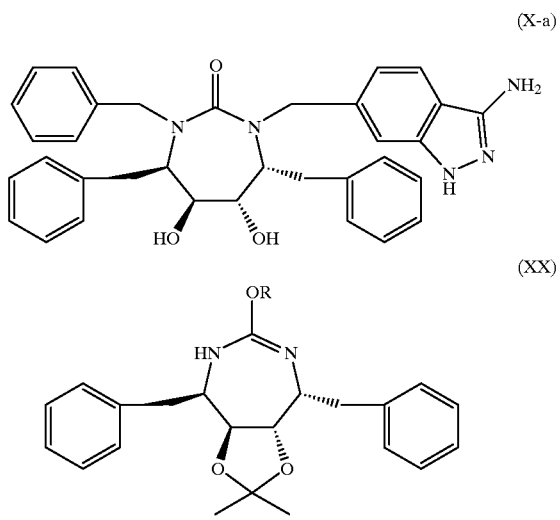

The isourea, (XX), can be used to prepare compounds of formula (X) which are unsymmetrical cyclic ureas.

A key intermediate in the synthesis of cyclic urea HIV protease inhibitors, such as (X-a), is the symmetrical diamine (I) (L. Rossano et al Tetrahedron. Lett., 1995, 36, 4967–4970).

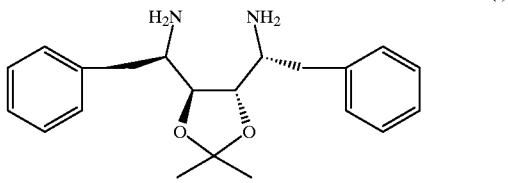

(I)

Methodology has been developed that allows for mono acylation of (I) enabling manipulation to unsymmetrical compounds such as (X-a). This mono acylation allows for the synthesis of unsymmetrical cyclic ureas by differentiating the symmetrical amines in (I). Additionally, mono acyl (I) can be prepared by first bis acylation of (I) followed by a selective hydrolysis to the same mono acyl derivative of (I).

T. Blacklock et al (*J. Org. Chem*, 1988, 53, 836–844) disclose the regioselective trifluoroacylation of L-lysine with ethyl trifluoroacetate in an aqueous sodium hydroxide medium using pH control to cause selective acylation. T. Shawe et al (*Synthetic Communications*, 1996, 26, 3633–3636) disclose the regiospecific trifluoroacylation of N-methylethylenediamine by reaction with ethyl trifluoroacetate; although this chemistry uses ethyl trifluoroacetate as the acylating agent, it is distinguishing a primary amine over a secondary amine where one would expect there to be a difference in reactivity between the amines based on steric arguments. These references teach acylation of diamino compounds wherein the diamines are non equivalent sterically and chemically.

D Xu et al (*Tetrahedron Letters*, 1995, 36, 7357–7360) disclose the mono-trifluoro acylation of diamines, wherein acylation occurs rapidly with one equivalent of acylating agent in a polar solvent such as tetrahydrofuran at or below 0° C. The authors describe mono acylation of a primary amine in a 1,2 diamine system wherein one amine acts as an internal base to activate the other amine. However, in the case of trans 1,2 diaminocyclohexane, a statistical mixture of diamine, mono-acylated and di-acylated material is obtained, indicating that no selectivity has occured. The authors postulate that this result is because one amine is not in close proximity to the other and so cannot promote acylation. Furthermore, the authors teach as the chain length between the amines increases, the degree of selectivity observed decreases.

The process of the present invention should not be amenable to selective acylation following the teachings of the literature, In the stereochemical configuration of diamine (I), the two primary amines have a trans configuration. Additionally, the diamines have a 1,4 relationship and thus there is an increase in the chain length between the amines. In addition, titration of (I) against hydrochloric acid reveals one inflection after two equivalents of acid have been added; because there is only one equivalence point, the two primary amines in (I) are not 'communicating' with each other thus one amine cannot be acting as an internal base. Lastly, the two primary amines in (I) are not differentiated sterically.

Experimentally, following the teachings of the literature, in the process of the invention the acylation of diamine (I) results in very little selectivity. The selective trifluoroacylation of (I) occurs with an excess of ethyl trifluoroacetate in a non-polar solvent such as toluene at elevated temperatures; the use of polar solvents, such as tetrahydrofuran, tend to degrade the selectivity.

Despite the various methods for their preparation, there still exists a need for more efficient and cost effective methods for the preparation of unsymmetrical N,N'-disubstututed cyclic urea HIV protease inhibitor compounds in high yield. The present invention provides improved processes for the synthesis of such compounds and processes for the synthesis of intermediates for their synthesis.

The diamine (I) is a key intermediate in the synthesis of unsymmetrical cyclic ureas that can be used as HIV protease inhibitors. This process allows the differentiation of the symmetrical primary amines in diamines of formula (I) in high yield. This process is suitable for large scale and is very volume efficient, providing excellent reactor through put in high yield and with low cost. The intermediates of the invention can be alkylated to give a wide range of unsymmetrical products which are useful as HIV protease inhibitors for the treatment of HIV infection. The dialkylated diamine intermediates of the invention provide starting materials, generally crystalline, suitable for large scale cyclization to cyclic ureas, which are, generally, crystalline.

The present invention provides an improved process for the cyclization of linear dialkylated diamines to cyclic ureas. Deleterious conditions of known processes are presented by an acid rearrangement mechanism, production to a high degree of byproduct, and the unsymmetrical amines of the substrate molecule. The present invention, through use of acid-base salt precipitates, unexpectedly improves upon the process by avoiding the acid rearrangement and minimizing the byproduct; therefore, resulting in a higher yield of cyclized urea in a process more suitable for large scale cyclization.

SUMMARY OF THE INVENTION

The present invention concerns an improved process for the preparation of asymmetric cyclic ureas as well as intermediates in the preparation of asymmetric cyclic ureas. In the process, a diamine of formula (I) is selectively monoacylated to give an asymmetric monoacylated diamine which can be converted into asymmetric intermediates, which can be further alkylated to give compounds which are useful as HIV protease inhibitors for the treatment of HIV infection. The invention allows for scalable preparation of a wide variety of asymmetric cyclic ureas. The processes of the invention can be conducted on a kilogram scale, provide for high yields, and yield stable intermediates.

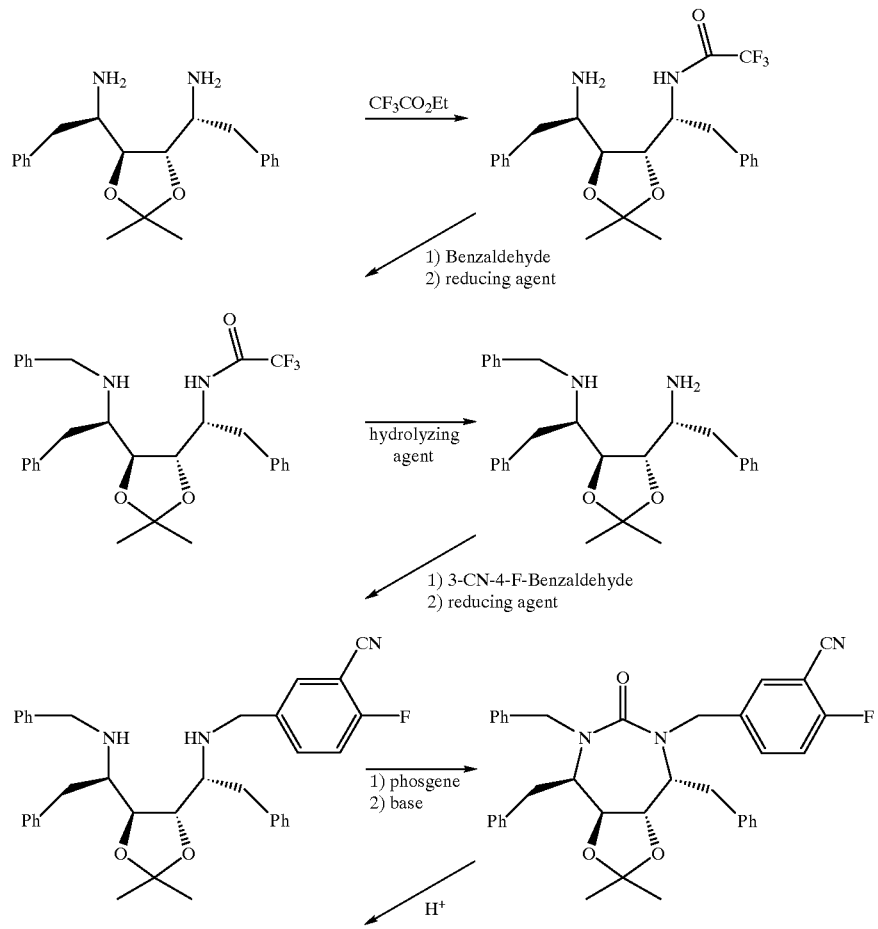

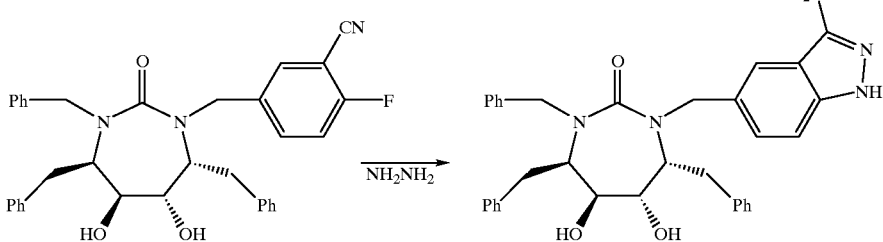

DETAILED DESCRIPTION OF THE INVENTION

In a first embodiment, the present invention provides a process for the preparation of compounds of formula (VI):

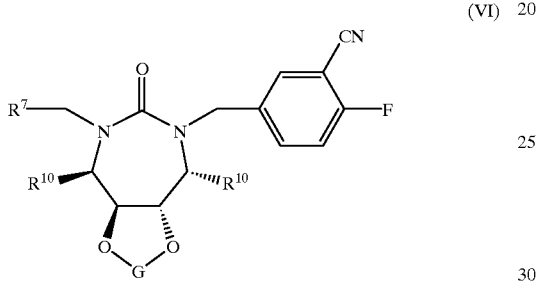

(VI)

wherein:
R$^7$ is selected from the following:
  C$_1$–C$_8$ alkyl substituted with 0–3 R$^{11}$;
  C$_2$–C$_8$ alkenyl substituted with 0–3 R$^{11}$;
  C$_2$–C$_8$ alkynyl substituted with 0–3 R$^{11}$; and
  a C$_3$–C$_{14}$ carbocyclic ring system substituted with 0–3 R$^{11}$;

R$^{10}$ is C$_1$–C$_{10}$ alkyl, benzyl, naphthylmethyl, 3,4-methylenedioxybenzyl, or C$_1$–C$_4$ alkyl substituted with phenyl wherein said phenyl is substituted with 0–3 R$^{10a}$;

R$^{10a}$ is C$_1$–C$_4$ alkyl, C$_1$–C$_4$ alkoxy, halo or cyano;

R$^{11}$ is selected from one or more of the following:
  C$_1$–C$_4$ alkoxy, C$_1$–C$_4$ alkyl, C$_2$–C$_6$ alkoxyalkyl, benzyl, phenethyl, phenoxy, benzyloxy, methylenedioxy, ethylenedioxy, C$_2$–C$_4$ alkenyl, C$_3$–C$_{10}$ cycloalkyl, C$_3$–C$_6$ cycloalkylmethyl, C$_3$–C$_6$ cycloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, 2-(1-morpholino)ethoxy;
  —C(=O)R$^{13}$, keto, cyano, nitro, —CH$_2$NR$^{13}$R$^{14}$, —NR$^{13}$R$^{14}$, —CO$_2$R$^{13}$, —OC(=O)R$^{13}$, —OR$^{13}$, —OCH$_2$CO$_2$R$^{13}$, —S(O)$_2$R$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$_{13}$, —SO$_2$NR$^{13}$R$^{14}$;
  C$_1$–C$_4$ alkyl substituted with —NR$^{13}$R$^{14}$; and
  C$_3$–C$_{14}$ carbocyclic residue substituted with 0–3 R$^{16}$;

R$^{13}$ is independently selected from:
  C$_1$–C$_6$ alkyl substituted with 0–3 R$^{15}$;
  C$_2$–C$_6$ alkenyl substituted with 0–3 R$^{15}$; and
  phenyl substituted with 0–3 R$^{16}$;

R$^{14}$ is independently selected from:
  C$_1$–C$_6$ alkoxy, C$_2$–C$_6$ alkenyl, phenyl, benzyl, and C$_1$–C$_6$ alkyl substituted with 0–3 C$_1$–C$_4$ alkoxy; or R$^{13}$ and R$^{14}$ can alternatively join to form —(CH$_2$)$_4$—, —(CH$_2$)$_5$—, —CH$_2$CH$_2$N(CH$_3$)CH$_2$CH$_2$—, or —CH$_2$CH$_2$OCH$_2$CH$_2$—;

R$^{15}$ is selected from one or more of the following:
  C$_1$–C$_4$ alkoxy, C$_1$–C$_4$ alkyl, C$_2$–C$_6$ alkoxyalkyl, benzyl, phenethyl, phenoxy, benzyloxy, methylenedioxy, ethylenedioxy, C$_2$–C$_4$ alkenyl, C$_3$–C$_{10}$ cycloalkyl, C$_3$–C$_6$ cycloalkylmethyl, C$_3$–C$_6$ cycloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, 2-(1-morpholino)ethoxy;
  —C(=O)R$^{23}$, cyano, nitro, —CH$_2$NR$^{23}$R$^{24}$, —NR$^{23}$R$^{24}$, —CO$_2$R$^{23}$, —OC(=O)R$^{23}$, —OR$^{23}$, —OCH$_2$CO$_2$R$^{23}$, —S(O)$_2$R$^{23}$, —C(=O)NR$^{23}$R$^{24}$, —NR$^{24}$C(=O)R$^{23}$, =NOR$^{24}$, —NR$^{24}$C(=O)OR$^{24}$, —OC(=O)NR$^{23}$R$^{24}$, —NR$^{23}$C(=O)NR$^{23}$R$^{24}$, —NR$^{24}$SO$_2$NR$^{23}$R$^{24}$, —NR$^{24}$SO$_2$R$^{23}$, —SO$_2$NR$^{23}$R$^{24}$;
  C$_1$–C$_4$ alkyl substituted with —NR$^{23}$R$^{24}$; and
  phenyl substituted with 0–3 R$^{16}$;

R$^{16}$ is selected from one or more of the following:
  H, halogen, cyano, nitro, —CH$_2$NR$^{23}$R$^{24}$, —NR$^{23}$R$^{24}$, —CO$_2$R$^{23}$, —OC(=O)R$^{23}$, —OR$^{23}$, —S(O)$_2$R$^{23}$, —C(=O)NR$^{23}$R$^{24}$, —NR$^{24}$C(=O)R$^{23}$, =NOR$^{24}$, —NR$^{24}$C(=O)OR$^{24}$, —OC(=O)NR$^{23}$R$^{24}$, —NR$^{23}$C(=O)NR$^{23}$R$^{24}$, —NR$^{24}$SO$_2$NR$^{23}$R$^{24}$, —NR$^{24}$SO$_2$R$^{23}$, —SO$_2$NR$^{23}$R$^{24}$;
  C$_1$–C$_4$ alkyl, C$_2$–C$_4$ alkenyl, C$_3$–C$_6$ cycloalkylmethyl, phenyl, benzyl, phenethyl, phenoxy, benzyloxy, C$_3$–C$_6$ cycloalkoxy, methylenedioxy, ethylenedioxy, C$_1$–C$_4$ alkoxycarbonyl, pyridylcarbonyloxy, C$_1$–C$_4$ alkylcarbonyl, C$_1$–C$_4$ alkylcarbonylamino, 2-(1-morpholino)ethoxy; and
  C$_1$–C$_4$ alkyl substituted with —NR$^{23}$R$^{24}$;

R$^{23}$ is C$_1$–C$_4$ alkyl substituted with 0–3 C$_1$–C$_4$ alkoxy;

R$^{24}$ is C$_1$–C$_4$ alkyl substituted with 0–3 C$_1$–C$_4$ alkoxy; or

R$^{23}$ and R$^{24}$ can alternatively join to form —(CH$_2$)$_4$—, —(CH$_2$)$_5$—, —CH$_2$CH$_2$N(CH$_3$)CH$_2$CH$_2$—, or —CH$_2$CH$_2$OCH$_2$CH$_2$—; and G taken together along with the oxygen atoms to which G is attached forms a group selected from:
  —O—C(—CH$_2$CH$_2$CH$_2$CH$_2$CH$_2$—)—O—, —O—C(CH$_2$CH$_3$)$_2$—O—, —O—C(CH$_3$)(CH$_2$CH$_3$)—O—, —O—C(CH$_2$CH$_2$CH$_2$CH$_3$)$_2$—O—, —O—C(CH$_3$)(CH$_2$CH(CH$_3$)CH$_3$)—O—, —O—CH(phenyl)—O—, —OCH$_2$O—, —OC(CH$_3$)$_2$O—, and —OC(OCH$_3$)(CH$_2$CH$_2$CH$_3$)O—;

said process comprising:

(1) contacting a compound of formula (I):

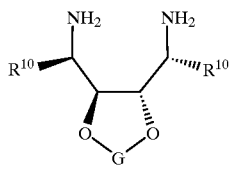
(I)

with an acylating agent of formula $R^1C(=O)R^2$;
wherein:

$R^1$ is $C_1$–$C_4$ haloalkyl;
$R^2$ is —$OR^3$, —$SR^3$, O-succinimide, or imidazolyl;
$R^3$ is selected from the group:
  $C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;
$R^{3a}$ is selected from the group:
  $C_1$–$C_4$ alkyl, $C_1$–$C_4$ alkoxy, halo, —CN, and —$NO_2$;
to form a compound of formula (II).

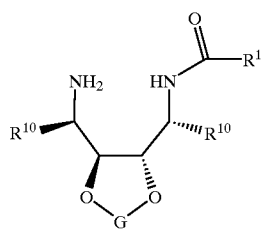
(II)

(2) contacting a compound of formula (II) with a compound of formula $R^7C(=O)H$ and subsequently contacting the imine product with a reducing agent to form a compound of formula (III):

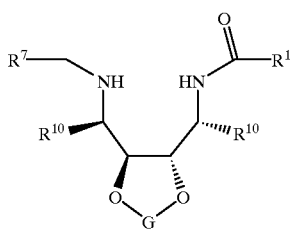
(III)

(3) contacting a compound of formula (III) with a suitable strong base at a temperature sufficient to form a compound of formula (IV):

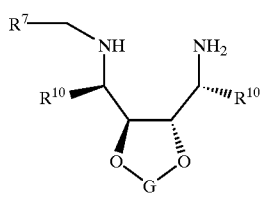
(IV)

(4) contacting a compound of formula (IV) with 3-nitrile-4-fluoro-benzaldehyde and subsequently contacting the imine product with a reducing agent to form a compound of formula (V):

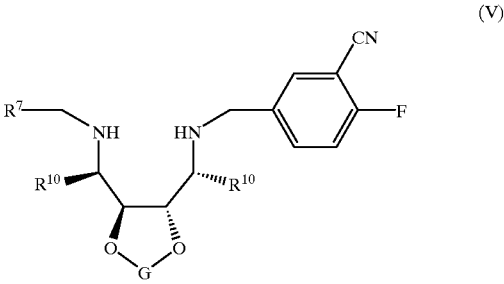
(V)

(5) contacting a compound of formula (V) with phosgene in the presence of a second suitable base to form a compound of formula (VI).

In a preferred embodiment, the present invention provides a process for the preparation of a compound of formula (VI) wherein:

$R^7$ is $C_1$–$C_8$ alkyl or phenyl;

the reducing agent of step (2) is selected from sodium triacetoxy borohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, and $H_2$/Raney®-Nickel;

the suitable strong base in step (3) is NaOH or KOH;

the reducing agent of step (4) is selected from sodium triacetoxy borohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, and $H_2$/Raney®-Nickel; and the suitable base in step (5) is selected from triethylamine, N,N-diisopropylethylamine, N,N-dimethyloctylamine, N,N,N',N'-tetramethylethylenediamine, tris(hydroxymethyl)aminomethane, and 1,8-bis(dimethylamino)napthalene.

In a more preferred embodiment, the present invention provides a process for the preparation of a compound of formula (VI) wherein:

the reducing agent of step (2) is sodium triacetoxy borohydride or $H_2$/Pt/C;

the suitable strong base in step (3) is NaOH or KOH;

the reducing agent of step (4) is sodium triacetoxy borohydride; and the suitable base in step (5) is tris(hydroxymethyl)aminomethane or N,N,N',N'-tetramethylethylenediamine.

In a second embodiment, the present invention provides a process for the preparation of a compound of formula (II):

(II)

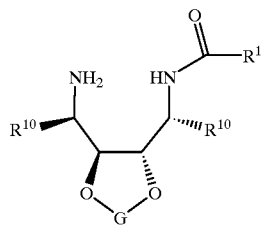

wherein:
R¹ is $C_1$–$C_4$ haloalkyl;
R¹⁰ is $C_1$–$C_{10}$ alkyl, benzyl, naphthylmethyl, 3,4-methylenedioxybenzyl, or $C_1$–$C_4$ alkyl substituted with phenyl wherein said phenyl is substituted with 0–3 $R^{10a}$;
$R^{10a}$ is $C_1$–$C_4$ alkyl, $C_1$–$C_4$ alkoxy, halo or cyano; and
G taken together along with the oxygen atoms to which G is attached forms a group selected from:
—O—C(—CH₂CH₂CH₂CH₂CH₂—)—O—, —O—C(CH₂CH₃)₂—O—, —O—C (CH₃) (CH₂CH₃)—O—, —O—C (CH₂CH₂CH₂CH₃)₂—O—, —O—C (CH₃) (CH₂CH(CH₃)CH₃)—O—, —O—CH(phenyl)—O—, —OCH₂O—, —OC(CH₃)₂O—, and —OC(OCH₃) (CH₂CH₂CH₃)O—;
the process, comprising:
(1) contacting a compound of formula (I):

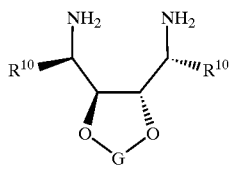

(I)

with an acylating agent of formula R¹C(=O)R²;
wherein:
R² is —OR³, —SR³, O-succinimide, or imidazolyl;
R³ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;
$R^{3a}$ is selected from the group:
$C_1$–$C_4$ alkyl, $C_1$–$C_4$ alkoxy, halo, —CN, and —NO₂;
to form a compound of formula (II).
In a preferred second embodiment, the present invention provides a process for the preparation of a compound of formula (II), wherein:
R¹ is —CF₃, —CF₂CF₃, —CF₂CF₂CF₃, —CF₂Cl, —CF₂Br, —CCl₃, —CBr₃, or CH₂F; and
R² is —OCH₃ or —OCH₂CH₃.
or wherein:
R¹ is —CF₃; and
R² is —OCH₃, —OCH₂CH₃, —OCH₂CH₂CH₃, —OCH(CH₃)₂, —OCH₂CH=CH₂, —OCH₂CF₃, —SCH₂CH₃, —O-phenyl, —O-(4-nitrophenyl), or —O-(2-pyridine).
In a more preferred second embodiment, the present invention provides a process for the preparation of a compound of formula (II) by contacting a compound of formula (II) with a suitable acid to form an acid addition salt.

In an even more preferred second embodiment, the present invention provides a process for the preparation of a compound of formula (II) wherein R¹ is $C_1$–$C_4$ haloalkyl;
the process, comprising:
(1) contacting a compound of formula (I):

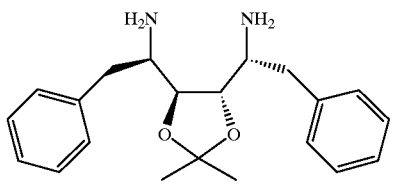

(I)

with an acylating agent of formula R¹C(=O)R²;
wherein:
R² is —OR³, —SR³, O-succinimide, or imidazolyl;
R³ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;
$R^{3a}$ is selected from the group:
$C_1$–$C_4$ alkyl, $C_1$–$C_4$ alkoxy, halo, —CN, and —NO₂;
to form a compound of formula (II).

In a third embodiment, the present invention provides a process for the preparation of a compound of formula (II):

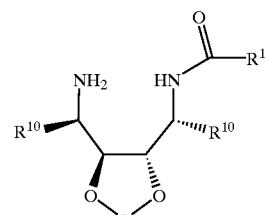

(II)

wherein:

R¹ is $C_1$–$C_4$ haloalkyl;
R¹⁰ is $C_1$–$C_{10}$ alkyl, benzyl, naphthylmethyl, 3,4-methylenedioxybenzyl, or $C_1$–$C_4$ alkyl substituted with phenyl wherein said phenyl is substituted with 0–3 $R^{10a}$;
$R^{10a}$ is $C_1$–$C_4$ alkyl, $C_1$–$C_4$ alkoxy, halo or cyano; and
G taken together along with the oxygen atoms to which G is attached forms a group selected from:
—O—C(—CH₂CH₂CH₂CH₂CH₂—)—O—, —O—C(CH₂CH₃)₂O—, —O—C(CH₃) (CH₂CH₃)—O—, —O—C(CH₂CH₂CH₂CH₃)₂—O—, —O—C(CH₃) (CH₂CH(CH₃)CH₃)—O—, —O—CH(phenyl)—O—, —OCH₂O—, —OC(CH₃)₂O—, and —OC(OCH₃) (CH₂CH₂CH₃)O—;

the process, comprising:

(1B) contacting a compound of formula (XI):

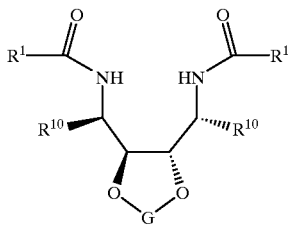

(XI)

with a suitable base to form a compound of formula (II).

In a preferred third embodiment, the present invention provides a process for the preparation of a compound of formula (II), wherein $R^1$ is —$CF_3$, —$CF_2CF_3$, —$CF_2CF_2CF_3$, —$CF_2Cl$, —$CF_2Br$, —$CCl_3$, —$CBr_3$, or $CH_2F$.

In a more preferred third embodiment, the present invention provides a process for the preparation of a compound of formula (II) wherein the suitable base in step (1B) is a hydroxide salt of sodium, potassium, lithium, calcium or magnesium; or a $C_1$–$C_{10}$ alkoxide salt of sodium, potassium, or lithium; or potassium t-butoxide in a mixture of tetrahydrofuran/methanol/water.

In an even more preferred third embodiment, the present invention provides a process for the preparation of a compound of formula (II) by further contacting a compound of formula (II) with a suitable acid to form an acid addition salt.

In an even more preferred embodiment, the present invention provides a process for the preparation of a compound of formula (II):

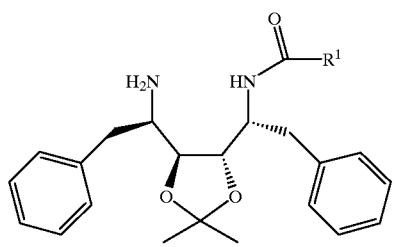

(II)

wherein $R^1$ is $C_1$–$C_4$ haloalkyl;
the process, comprising:
(1B) contacting a compound of formula (XI):

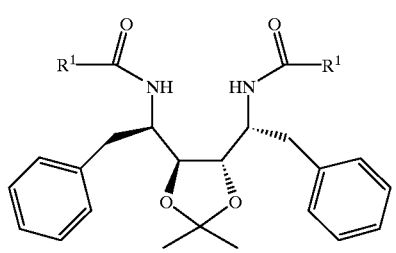

(XI)

with a suitable base to form a compound of formula (II).

In a fourth embodiment, the present invention provides a process for the preparation of a compound of formula (VI):

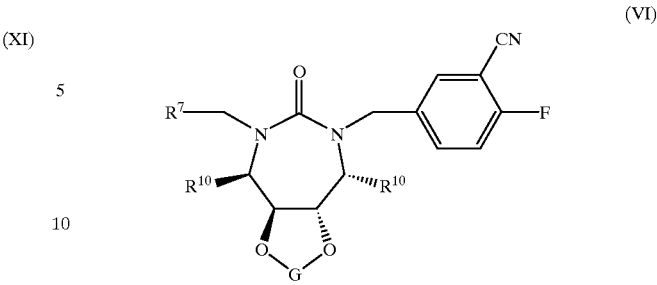

(VI)

wherein:
$R^7$ is selected from the following:
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$; and
  a $C_3$–$C_{14}$ carbocyclic ring system substituted with 0–3 $R^{11}$;
$R^{10}$ is $C_1$–$C_{10}$ alkyl, benzyl, naphthylmethyl, 3,4-methylenedioxybenzyl, or $C_1$–$C_4$ alkyl substituted with phenyl wherein said phenyl is substituted with 0–3 $R^{10a}$;
$R^{10a}$ is $C_1$–$C_4$ alkyl, $C_1$–$C_4$ alkoxy, halo or cyano;
$R^{11}$ is selected from one or more of the following:
  $C_1$–$C_4$ alkoxy, $C_1$–$C_4$ alkyl, $C_2$–$C_6$ alkoxyalkyl, benzyl, phenethyl, phenoxy, benzyloxy, methylenedioxy, ethylenedioxy, $C_2$–$C_4$ alkenyl, $C_3$–$C_{10}$ cycloalkyl, $C_3$–$C_6$ cycloalkylmethyl, $C_3$–$C_6$ cycloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy;
  —$C(=O)R^{13}$, keto, cyano, nitro, —$CH_2NR^{13}R^{14}$, —$NR^{13}R^{14}$, —$CO_2R^{13}$, —$OC(=O)R^{13}$, —$OR^{13}$, —$OCH_2CO_2R^{13}$, —$S(O)_2R^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$;
  $C_1$–$C_4$ alkyl substituted with —$NR^{13}R^{14}$; and
  $C_3$–$C_{14}$ carbocyclic residue substituted with 0–3 $R^{16}$;
$R^{13}$ is independently selected from:
  $C_1$–$C_6$ alkyl substituted with 0–3 $R^{15}$;
  $C_2$–$C_6$ alkenyl substituted with 0–3 $R^{15}$; and
  phenyl substituted with 0–3 $R^{16}$;
$R^{14}$ is independently selected from:
  $C_1$–$C_6$ alkoxy, $C_2$–$C_6$ alkenyl, phenyl, benzyl, and $C_1$–$C_6$ alkyl substituted with 0–3 $C_1$–$C_4$ alkoxy; or
$R^{13}$ and $R^{14}$ can alternatively join to form —$(CH_2)_4$—, —$(CH_2)_5$—, —$CH_2CH_2N(CH_3)CH_2CH_2$—, or —$CH_2CH_2OCH_2CH_2$—;
$R^{15}$ is selected from one or more of the following:
  $C_1$–$C_4$ alkoxy, $C_1$–$C_4$ alkyl, $C_2$–$C_6$ alkoxyalkyl, benzyl, phenethyl, phenoxy, benzyloxy, methylenedioxy, ethylenedioxy, $C_2$–$C_4$ alkenyl, $C_3$–$C_{10}$ cycloalkyl, $C_3$–$C_6$ cycloalkylmethyl, $C_3$–$C_6$ cycloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy;
  —$C(=O)R^{23}$, cyano, nitro, —$CH_2NR^{23}R^{24}$, —$NR^{23}R^{24}$, —$CO_2R^{23}$, —$OC(=O)R^{23}$, —$OR^{23}$, —$OCH_2CO_2R^{23}$, —$S(O)_2R^{23}$, —$C(=O)NR^{23}R^{24}$, —$NR^{24}C(=O)R^{23}$, =$NOR^{24}$, —$NR^{24}C(=O)OR^{24}$, —$OC(=O)NR^{23}R^{24}$, —$NR^{23}C(=O)$ $NR^{23}R^{24}$, $-NR^{24}SO_2NR^{23}R^{24}$, $-NR^{24}SO_2R^{23}$, $-SO_2NR^{23}R^{24}$;

$C_1$–$C_4$ alkyl substituted with $-NR^{23}R^{24}$; and phenyl substituted with 0–3 $R^{16}$;

$R^{16}$ is selected from one or more of the following:

H, halogen, cyano, nitro, $-CH_2NR^{23}R^{24}$, $-NR^{23}R^{24}$, $-CO_2R^{23}$, $-OC(=O)R^{23}$, $-OR^{23}$, $-S(O)_2R^{23}$, $-C(=O)NR^{23}R^{24}$, $-NR^{24}C(=O)R^{23}$, $=NOR^{24}$, $-NR^{24}C(=O)OR^{24}$, $-OC(=O)NR^{23}R^{24}$, $-NR^{23}C(=O)NR^{23}R^{24}$, $-NR^{24}SO_2NR^{23}R^{24}$, $-NR^{24}SO_2R^{23}$, $-SO_2NR^{23}R^{24}$;

$C_1$–$C_4$ alkyl, $C_2$–$C_4$ alkenyl, $C_3$–$C_6$ cycloalkylmethyl, phenyl, benzyl, phenethyl, phenoxy, benzyloxy, $C_3$–$C_6$ cycloalkoxy, methylenedioxy, ethylenedioxy, $C_1$–$C_4$ alkoxycarbonyl, pyridylcarbonyloxy, $C_1$–$C_4$ alkylcarbonyl, $C_1$–$C_4$ alkylcarbonylamino, 2-(1-morpholino)ethoxy; and $C_1$–$C_4$ alkyl substituted with $-NR^{23}R^{24}$;

$R^{23}$ is $C_1$–$C_4$ alkyl substituted with 0–3 $C_1$–$C_4$ alkoxy;

$R^{24}$ is $C_1$–$C_4$ alkyl substituted with 0–3 $C_1$–$C_4$ alkoxy; or $R^{23}$ and $R^{24}$ can alternatively join to form $-(CH_2)_4-$, $-(CH_2)_5-$, $-CH_2CH_2N(CH_3)CH_2CH_2-$, or $-CH_2CH_2OCH_2CH_2-$; and G taken together along with the oxygen atoms to which G is attached forms a group selected from:

$-O-C(-CH_2CH_2CH_2CH_2CH_2-)-O-$, $-O-C(CH_2CH_3)_2-O-$, $-O-C(CH_3)(CH_2CH_3)-O-$, $-O-C(CH_2CH_2CH_2CH_3)_2-O-$, $-O-C(CH_3)(CH_2CH(CH_3)CH_3)-O-$, $-O-CH(phenyl)-O-$, $-OCH_2O-$, $-OC(CH_3)_2O-$, and $-OC(OCH_3)(CH_2CH_2CH_3)O-$;

said process comprising:

(5) contacting a compound of formula (V):

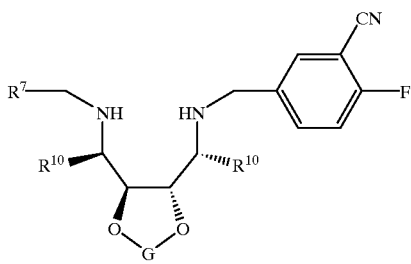

(V)

with a cyclizing agent selected from phosgene, diphosgene, and triphosgene, in the presence of a suitable base to form compound of formula (VI).

In a preferred fourth embodiment, the present invention provides a process for the preparation of a compound of formula (VI) wherein $R^7$ is $C_1$–$C_8$ alkyl or phenyl;

said process comprising:

(5) contacting a compound of formula (V) with a cyclizing agent selected from phosgene, diphosgene, and triphosgene, in the presence of a suitable base to form a compound of formula (VI).

In a more preferred fourth embodiment, the present invention provides a process for the preparation of a compound of formula (VI) wherein the suitable base in step (5) is selected from triethylamine, N,N-diisopropylethylamine, N,N-dimethyloctylamine, N,N,N',N'-tetramethylethylenediamine, tris(hydroxymethyl) aminomethane, and 1,8-bis(dimethylamino)napthalene.

In a fifth embodiment, the present invention provides compounds of formula

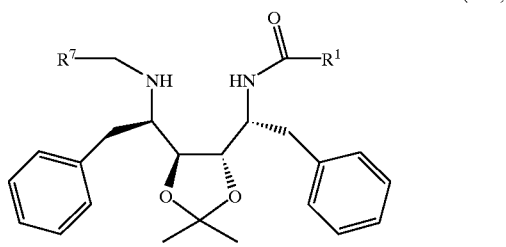

(III-a)

and acid addition salts thereof, wherein:

$R^1$ is $-CF_3$, $-CF_2CF_3$, $-CF_2CF_2CF_3$, $-CF_2Cl$, $-CF_2Br$, $-CCl_3$, $-CBr_3$ or $CH_2F$; and $R^7$ is propyl or phenyl.

In a sixth embodiment, the present invention provides compounds of formula

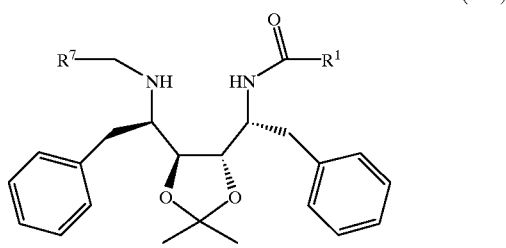

(III-a)

and acid addition salts thereof, wherein:

$R^1$ is $-CF_3$, $-CF_2CF_3$, $-CF_2CF_2CF_3$, $-CF_2Cl$, $-CF_2Br$, $-CCl_3$, $-CBr_3$ or $CH_2F$; and $R^7$ is propyl or phenyl.

In a seventh embodiment, the present invention provides compounds of formula

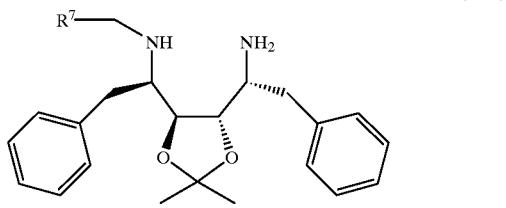

(IV-a)

and acid addition salts thereof, wherein $R^7$ is propyl or phenyl.

In a eighth embodiment, the present invention provides compounds of formula

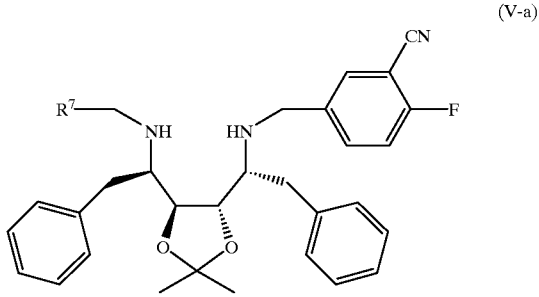

(V-a)

and acid addition salts thereof wherein $R^7$ is propyl or phenyl.

In a ninth embodiment, the present invention provides a process for the preparation of a compound of formula (X):

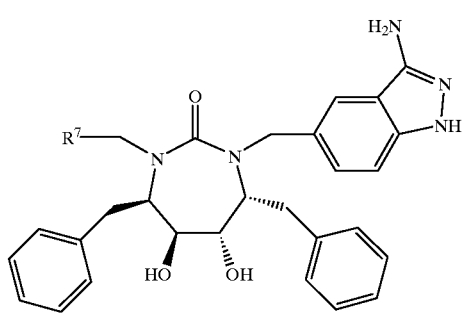

(X)

comprising contacting a compound of formula (VI) with hydrazine, or a hydrazine equivalent, under conditions sufficient to form a compound of formula (X), or a pharmaceutically acceptable salt form thereof; wherein a condition sufficient to form a compound of formula (X) comprises:

(a) removing the diol protecting group G of formula (VI) before contacting a compound of formula (VI) with hydrazine, or a hydrazine equivalent; or (b) removing the diol protecting group G of formula (VI) after contacting a compound of formula (VI) with hydrazine, or a hydrazine equivalent.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

As used herein, suitable aprotic solvents include, by way of example and without limitation, ether solvents and hydrocarbon solvents. Suitable ether solvents include tetrahydrofuran, diethyl ether, diethoxymethane, ethylene glycol dimethyl ether, ethylene glycol diethyl ether, diethylene glycol dimethyl ether, diethylene glycol diethyl ether, triethylene glycol dimethyl ether, or t-butyl methyl ether. Suitable hydrocarbon solvents include: butane, pentane, hexane, heptane, octane, nonane, decane, cyclohexane, cycloheptane, methylcyclohexane; as well as aryl hydrocarbon solvents.

As used herein, suitable acetate solvents include methyl, ethyl, propyl and iso-propyl acetate.

As used herein, suitable halogenated sol anded to chlorobutane, methylene chloride, chloroform, dichloroethane, and carbon tetrachloride.

As used herein, suitable aryl solvents include toluene, benzene, o-xylene, m-xylene and p-xylene.

As used herein the term "acylating agent" or "strongly electrophilic acylating agent" refers to any agent which can acylate a primary amine. "Acylating agent" generally refers to agents of formula $R^1C(=O)R^2$ which can selectively acylate one primary amine in the presence of a second primary amine. Examples of acylating agents include $R^2$ as an alkoxy or phenoxy group and $R^1$ as a $C_1-C_4$ haloalkyl group, such as $CF_3$, $CF_2CF_3$, $CF_2CF_2CF_3$, $CF_2Cl$, $CF_2Br$, $CCl_3$, $CBr_3$, or $CH_2F$. "Strongly electrophilic acylating agent" generally refers to agents which can nonselectively acylate two primary amines in one molecule, for example anhydrides of formula, $R^1(CO)O(CO)R^1$, or $R^1$ substituted acid halides, eg. $R^1C(=O)Cl$, but may also include acylating agents of formula $R^1C(=O)R^2$ depending on the reaction conditions as determined by one of skill in the art to synthesize a compound of formula (II). Examples of strongly electrophilic acylating agents are where $R^1$ is a $C_1-C_3$ haloalkyl, such as $CF_3$, $CF_2CF_3$, $CF_2CF_2CF_3$, $CF_2Cl$, $CF_2Br$, $CCl_3$, $CBr_3$, or $CH_2F$.

As used herein, the term "reducing agent" refers to any agent which can effect the reduction of an imine to an amine without effecting a chemical change on any other substitutents on the diamine substrate. Examples of reducing agents include hydrogen metal catalysts, chemical reducing agents, and catalytic transfer hydrogenation. Examples of hydrogen metal catalysts include, but are not limited to, Pd/C, Pt/C, Rh/C, and Raney-Nickel. Examples of chemical reducing agents include, but are not limited to, sodium triacetoxy borohydride, sodium borohydride, pyridine/borane, lithium aluminium hydride, lithium borohydride, sodium cyanoborohydride, and sodium amalgam.

As used herein, the term "hydrolyzing agent" means a reagent capable of generating sufficient hydroxide ion in solution to remove the acyl group from a compound of formula (III). Examples of suitable hydrolyzing agents include but are not limited to sodium hydroxide in methanol, potassium hydroxide in isopropanol and potassium hydroxide in n-butanol.

As used herein, the term "cyclizing agent" means a reagent that can effect the formation of a cyclic urea from the diamine of formula (V). Examples of suitable cyclizing agents include but are not limited to phosgene, diphosgene, triphosgene, 1,1'-carbonyl diimidazole, phenyl chloroformate, 4-nitro-phenyl chloroformate, phenyl tetrazoylformate, oxalyl chloride, N,N'-disuccinimidyl carbonate, trichloromethyl chloroformate, $C_1-C_4$ dialkyl carbonate, ethylene carbonate, vinylene carbonate, and 2(S),3 pyridinediyl carbonate.

As used herein, "alkyl" is intended to include both branched and straight chain saturated aliphatic hydrocarbon groups having one to twelve carbon atoms; for example, $C_1-C_4$ alkyl includes methyl, ethyl, n-propyl, i-propyl, n-butyl, i-butyl, s-butyl, and t-butyl. "Alkenyl" is intended to include hydrocarbon chains of either a straight or branched configuration and one or more unsaturated carbon-carbon bonds which may occur in any stable point along the chain, such as ethenyl, 1-propenyl, 2-propenyl, 1-butenyl, 2-butenyl, 3-butenyl, 1,3-butadienyl and the like; and "alkynyl" is intended to include hydrocarbon chains of either a straight or branched configuration and one or more triple carbon-carbon bonds which may occur in any stable point along the chain, such as ethynyl, propynyl, butynyl and the like.

As used herein, "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl.

As used herein, "carbocycle" or "carbocyclic" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein "halo" or "halogen" refers to fluoro, chloro, bromo and iodo.

As used herein "haloalkyl" is intended to include both branched and straight-chain saturated aliphatic hydrocarbon groups having the specified number of carbon atoms, substituted with 1 or more halogen. For example, $C_1$–$C_4$ haloalkyl includes, but is not limited to, $CF_3$, $CF_2CF_3$, $CF_2CF_2CF_3$, $CF_2CF_2CF_2CF_3$, $CF_2Cl$, $CF_2Br$, $CCl_3$, $CBr_3$, $CH_2F$, $CH_2CF_3$, and the like.

As used herein "alkoxy" represents an alkyl group of indicated number of carbon atoms attached through an oxygen bridge. For example $C_1$–$C_4$ alkoxy includes methoxy, ethoxy, propoxy and butoxy. As used herein "cycloalkoxy" represents a cycloalkyl group of indicated number of carbon atoms attached through an oxygen bridge. For example $C_3$–$C_6$ cycloalkoxy includes cyclopropyloxy, cyclobutyloxy, cyclopentyloxy, and cyclohexyloxy.

As used herein "alkylcarbonyl" is intended to include an alkyl group of an indicated number of carbon atoms attached through a carbonyl group to the residue of the compound at the designated location. For example $C_1$–$C_4$ alkylcarbonyl includes methylcarbonyl, ethylcarbonyl, propylcarbonyl and butylcarbonyl.

As used herein "alkylcarbonyloxy" is intended to include an alkyl group of an indicated number of carbon atoms attached to a carbonyl group, where the carbonyl group is attached through an oxygen atom to the residue of the compound at the designated location.

As used herein "alkylcarbonylamino" is intended to include an alkyl group of an indicated number of carbon atoms attached to a carbonyl group, where the carbonyl group is attached through an amino group to the residue of the compound at the designated location.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contain a basic or acidic moiety by conventional chemical methods. Generally, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

It is understood that where the processes of the invention describe the use of a suitable acid to form an acid addition salt, one of skill in the art of synthesis can use an inorganic or an organic acid which could also render a pharmaceutically acceptable salt. In addition to the acids listed above for pharmaceutically acceptable salts the following acids are examples of suitable acids for the formation of an acid addition salt: phthalic acid, salicylic acid, isophthalic acid, and malonic acid.

As used herein, suitable recrystallization solvents include those in which the product will dissolve when heated and crystallize when cooled. Examples include, but are not limited to alkanes, ethers, esters (acetates), alcohols, aryls, halogenated alkanes, organic acids and water.

When any variable (for example, $R^{10a}$, $R^{3a}$, etc.) occurs more than one time in any constituent or formula for a compound, its definition on each occurrence is independent of its definition at every other occurrence. Thus, for example, if a group is shown to be substituted with 0–3 $R^{10a}$, then said group may optionally be substituted with up to three $R^{10a}$ and $R^{10a}$ at each occurrence is selected independently from the defined list of possible $R^{10a}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —$C(R^{10a})_2$—, each of the two $R^{10a}$ substituents on C is independently selected from the defined list of possible $R^{10a}$.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The following terms and abbreviations are used herein and defined as follows. The abbreviation: "THF" as used herein means tetrahydrofuran, "HPLC" as used herein means high performance liquid chromatograpy, "TLC" as used herein means thin layer chromatography, "liq" as used herein means liquid, "n-BuOH" as used herein means n-butanol and "TMEDA" as used herein means N,N,N',N'-tetramethylethylenediamine.

The methods of the present invention, by way of example and without limitation, may be further understood by reference to Scheme 1. Scheme 1 details the general synthetic method for the preparation of asymmetric cyclic ureas starting from monoacylation of a 1,4-diaminobutane. In Scheme 1, $R^{10}$ is a substituted or unsubstituted benzyl group and G is a diol protecting group.

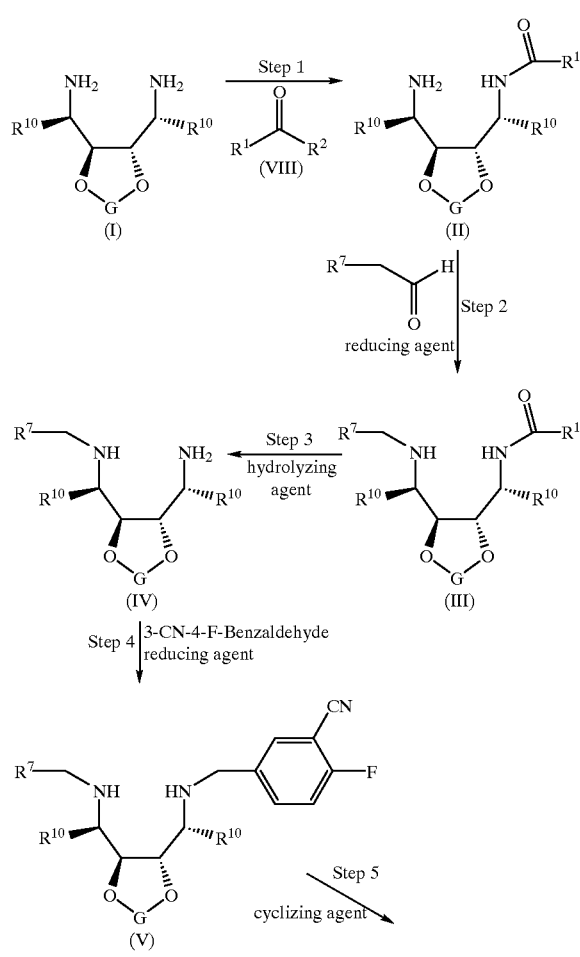

Scheme 1

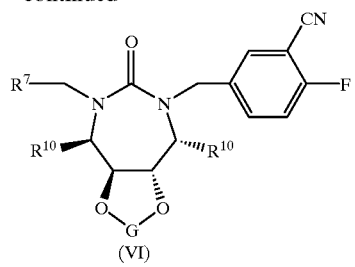

Step 1: Monoacylation: Preparation of a Compound of Formula (II).

This step is conducted by reacting a diamine of formula (I) with an acylating agent, $R^1C(=O)R^2$, to form a monoacylated compound, (II), which can be used as is or can be reacted with a suitable acid to form an isolable acid addition salt. By way of general guidance, at least one equivalent, preferably one to two, more preferably 1.4 to 1.6 equivalents, of an acylating agent is added to a solution of compound (I) in a suitable solvent; while stirring at a suitable temperture the reaction is monitered for completion by HPLC analysis of reaction samples. Upon completion of the reaction, monoacylated compound, (II), can be isolated as a free base or as an acid addition salt by separation methods known to one skilled in the art. Separation methods and examples of standard work up are shown in Examples 1–8. Preferably, the free base is obtained by distilling off the acylating agent or the acid addition salt is obtained by addition of a suitable acid which results in precipitation of the acid addition salt. More preferably, the monoacylated compound, (II), is isolated as the phthalate salt from a mixture of toluene and isopropanol. The phthalic acid salt can be recrystallised from acetonitrile if further purification is required.

In Step 1 the reaction is considered complete by HPLC analysis when the ratio of the area percent product to area percent starting material is at least 10:1; preferably greater than 12:1; more preferably greater than 15:1.

Suitable solvents for the reaction of (I) with the acylating agent in step (1) are non-polar solvents such as toluene, methyl-t-butyl ether, cyclohexane, hexane, and heptane; most preferably toluene. The suitable acid in step (1) can be added neat, for example as a solid, as a suspension in a second solvent, or as a solution in a second solvent, selected by one of skill in the art; preferably an organic solvent miscible with the reaction solvent; more preferably isopropanol.

It is understood that a large scope of acylating agents, $R^1C(=O)R^2$, are suitable for this reaction. It is prefered that $R^2$ is an alkoxy or phenoxy group, such as methoxy, ethoxy, propoxy, isopropoxy, butoxy, phenoxy, and equivalents thereof; and that $R^1$ is a $C_1$–$C_4$ haloalkyl, preferably $C_1$–$C_3$ haloalkyl, such as $CF_3$, $CF_2CF_3$, $CF_2CF_2CF_3$, $CF_2Cl$, $CF_2Br$, $CCl_3$, $CBr_3$, or $CH_2F$. More preferably the acylating agent is $F_3CC(=O)OCH_2CH_3$.

A suitable temperature for the monoacylation reaction is from about 0° C. to reflux of the solvent. The preferred temperature depends on the acylating agent, for example with $F_3CC(=O)OCH_2CH_3$ the preferred range is 40–50° C.; and is readily determined by one skilled in the art.

It is understood that one skilled in the art can determine the preferred reaction time of Step (1) as dependent on acylating agent and temperature of the reaction. For example with $F_3CC(=O)O(p-C_6H_4NO_2)$ the reaction can be complete within 5 minutes at 0° C. However, with $Cl_3CC(=O)$ OCH$_2$CH$_3$ the reaction was heated at 110° C. for three days. Preferably the reaction is complete in less than twenty four hours; more preferably reaction is complete within 4–5 hours at 40–50° C., for example when F$_3$CC(=O)OCH$_2$CH$_3$ is the acylating agent.

Suitable acids for the preparation of the acid addition salt are phthalic acid, salicylic acid, isophthalic acid, malonic acid; preferably phthalic acid.

The reaction carried out in Step 1 has been run on various scales in kilo laboratory glassware and pilot plant scale.

Step 2: Reductive Amination: Preparation of a Compound of Formula (III).

This step is conducted by reacting an aldehyde of formula R$^7$CH$_2$CHO with a compound of formula (II) to form an imine which is subsequently reduced to a compound of formula (III) by a suitable reducing agent. By way of general guidance, compound (II) is dissolved in an organic solvent and neutralized by the addition of aqueous hydroxide solution (sodium or potassium) if the acid addition salt of (II) is used. The reaction is dried, for example by extraction and azeotropic distillation, afterwhich about one equivalent of R$^7$CH$_2$CHO is added to form the imine intermediate. Formation of the imine intermediate can be driven by additional drying of the reaction solvent by methods known to one skilled in the art, such as molecular sieves (for example 4 Å sieves) or distillation, preferably via azeotropic removal of water. Subsequently, the imine is reduced by addition of a suitable reducing agent to form compound (III) which can be isolated by standard methods of work up. Examples of work up are given in Example 19, 19a, and 19b. It is optional that compound (III) can be isolated as an acid addition salt.

Suitable organic solvents for step 2 are toluene, cyclohexane, hexane, heptane, isopropyl acetate, and ethyl acetate; more preferably toluene.

The imine intermediate can be reduced to (III) with a variety of suitable reducing agents, such as, hydrogen metal catalysts, chemical reducing agents, and catalytic transfer hydrogenation.

For reductions using hydrogen preferred metal catalysts are Pd/C, Pt/C, Rh/C, and Raney®-Nickel (aluminum nickel catalyst. Additionally, preferred solvents for reductions using hydrogen metal catalysts are methanol, ethanol, isopropanol, cyclohexane, toluene, tetrahydrofuran, ethyl acetate, isopropyl acetate or acetonitrile.

For reductions using chemical reducing agents preferred agents are sodium triacetoxy borohydride, sodium borohydride, pyridine/borane, lithium aluminium hydride, lithium borohydride, sodium cyanoborohydride, and sodium amalgam. Preferred solvents for reductions using chemical reducing agents are toluene, cyclohexane, methanol, ethanol, tetrahydrofuran and ether.

It is understood that one skilled in the art of organic synthesis will judiciously choose a suitable reducing agent based on the stability of R$^7$ substituents on the aldehyde. For example, when R$^7$ is propyl, it is more preferred that the reducing agent is 10% Pd/C in toluene. However, when R$^7$ is phenyl, it is more preferred that the reducing agent is 5% Pt/C in methanol or ethanol between 25–45° C. or sodium triacetoxy borohydride in toluene or cyclohexane between 25–45° C.

It is understood that the acid addition salt of (III), if prepared, can be prepared from a number of suitable acids known to and judiciously chosen by one skilled in the art. Preferred acids are para-toluene sulphonic acid or methanesulfonic acid. For example, when R$^7$ is phenyl, paratoluene sulphonic acid is preferred; and when R$^7$ is propyl, methane sulphonic acid is preferred. Additionally, the acid addition salt of (III) can be prepared in a number of solvents; preferred solvents include ethyl acetate, isopropyl acetate or a mixture of cyclohexane and isopropanol.

The reaction carried out in Step 2 has been run on a kilogram scale.

Step 3: De-acylation: Preparation of a Compound of Formula (IV).

This step is conducted by reacting a compound of formula (III) as prepared in Step 2 with a suitable hydrolyzing agent under forcing conditions to form the primary amine compound of formula (IV). By way of general guidance, the protecting group is removed by hydrolysis wherein hydroxide ion in an alcohol solvent is preferred under refluxing conditions. Compound (IV) can be isolated or carried forward into Step 4.

Preferred hydrolyzing agents are sources of hydroxide ion in an alcohol solvent and include sodium hydroxide in methanol, potassium hydroxide in isopropanol and potassium hydroxide in n-butanol. A more preferable condition is isopropanol with 4 equivalents of potassium hydroxide at reflux.

Step 4: Reductive Amination: Preparation of a Compound of Formula (V).

This step is conducted by reacting 3-nitrile,4-fluoro benzaldehyde with a compound of formula (IV) to form an imine which is subsequently reduced by a suitable reducing agent to form a compound of formula (V); as similarly described in Step 2. By way of general guidance, about one equivalent of 3-nitrile,4-fluoro benzaldehyde is contacted with a compound of formula (IV) to form an imine intermediate, wherein azeotropic distillation of the water formed is preferred. The imine formed is contacted with a about 1 to about 3 equivalents of a suitable reducing agent, preferably a chemical reducing agent, more preferably sodium triacetoxy borohydride in toluene or cyclohexane between 25–45° C. to form a compound of formula (V). The product can be isolated by standard methods of work up as shown in Example 20 and 20a. It is preferred that the compound of formula (V) is isolated and purified by recrystalising from n-heptane, hexane(s) or cyclohexane; more preferably n-heptane.

The reaction carried out in Step 4 has been run on a kilogram scale.

Step 5: Cyclization: Preparation of a Compound of Formula (VI).

This step is conducted by reacting a diamine compound of formula (V) with a cyclizing agent in the presence of a suitable base to form a compound of formula (VI). By way of general guidance a diamine compound of formula (V) and about 1.2 to about 3.0 equivalents, preferably 1.2 to 2.0 equivalents, of a suitable base are dissolved under reflux into a suitable solvent. About 0.4 to about 3.0 equivalents of cyclizing agent, depending on the equivalents of base, dissolved into the same suitable solvent are added subsurface, over a controlled period of time, to the refluxing mixture of compound (V) and base. During the addition of cyclizing agent the total volume of refluxing solution may be controlled by distilling off the solvent such that the maximum volume of refluxing solution is about 0.10 molar to about 0.13 molar, preferably 0.11 to 0.12 molar, in relation to compound (V). Upon complete addition of the cyclizing agent the reaction is cooled, the base-HCl salt formed removed, preferably by filtration or extraction, and the product compound (VI) isolated. Examples of workup are shown in Examples 22 and 22a.

Optionally, the cyclic urea (VI) can either be isolated and then deprotected, or subjected in situ to acidic conditions to remove the protecting group G to form compounds of Formula (VII). Methanolic hydrochloric acid or sulphuric acid is preferred to remove the diol protecting group G to form the free diol; whereupon the free diol generally crystallizes from the reaction mixture or can be isolated by methods known to one skilled in the art. Preferably, the protecting group G is acetonide.

The base is used to scavenge hydrochloric acid that is generated during the reaction and generally a non nucleophilic or weakly nucleophilic base can be used. Preferred suitable bases include N,N-diisopropylethylamine, triethylamine, N,N,N',N'-tetramethylethylenediamine, N,N-dimethyloctylamine, tris(hydroxymethyl)aminomethane, and 1,8-bis(dimethylamino)napthalene. More preferable is N,N,N',N'-tetramethylethylenediamine or tris(hydroxymethyl)aminomethane as the base. Most preferrable is tris(hydroxymethyl)aminomethane.

A suitable aprotic solvent for this step includes: benzene, cyclohexane, pentane, hexane, toluene, methylcyclohexane, heptane, ethylbenzene, m-, o-, or p-xylene, octane, indane, nonane, naphthalene, tetramethylurea, nitromethane, nitrobenzene, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether, carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene.

Preferred solvents for step 5 include toluene, cyclohexane, chlorobenzene, 1,2-dichlorobenzene, and anisole. The more preferred solvent is toluene.

Preferred cyclizing agents for Step 5 are phosgene, diphosgene, and triphosgene; more preferred is 1.0–3.0 equivalents phosgene and about 0.4–0.6 equivalents of triphosgene; most preferred is 1.2–2.0 equivalents of phosgene.

The reaction carried out in Step 5 has been run on a kilogram scale.

Step 6: Preparation of Compounds of Formula (X); Amino Indazolyl Formation and Alcohol Deprotection.

This step is conducted by reacting a compound of formula (VI) or (VII) with hydrazine or a hydrazine equivalent in the presence of a base, such base being suitable for scavenging HF produced in the reaction, to form an amino indazolyl derivative of a compound of formula (VI) or (VII). Amino indazolyl derivatives of a compound of formula (VI) have an alcohol protecting group G which can be removed by conditions described in Step 5 above, ie acidic conditions, to form a compound of formula (X). Amino indazolyl derivatives of a compound of formula (VII) have already been alcohol deprotected as described by conditions in Step 5 above, ie acidic conditions, and therefore form a compound of formula (X) upon reaction with hydrazine or a hydrazine equivalent. By way of general guidance one equivalent of a compound of formula (VI) or (VII) is reacted with at least one equivalent to an excess, preferably at least two equivalents, more preferably at least five equivalents of hydrazine or a hydrazine equivalent in the presence of an HF scavenging base. Examples are shown in Examples 23 and 23a.

Bases suitable for scavenging HF are inorganic as well as organic bases. Preferred bases are carbonate salts such as potassium carbonate, cesium carbonate, and calcium carbonate. A more preferred base used to scavenge hydrofluoric acid is calcium carbonate. Optionally, hydrazine itself may function as the base to scavenge HF produced.

A suitable solvent for this step includes: low molecular weight alcohols, such as ethanol, propanol, butanol, pentanol, and hexanol; and ethers, such as tetrahydrofuran. Preferred is 2-propanol or n-butanol. Optionally, hydrazine itself may function as the solvent.

Hydrazine equivalents for this step include anhydrous hydrazine, hydrazine hydrate, and salts of hydrazine, such as hydrazine acetate, hydrazine bromide, hydrazine hydrochloride, and hydrazine sulfate. It is understood by one skilled in the art that when hydrazine salts are used an additional quantity of base must be used to neutralize the acid of the hydrazine salt. Preferred is hydrazine hydrate.

The reaction carried out in Step 6 has been run on a kilogram scale.

The present invention, by way of example and without limitation, may be further exemplified by reference to Scheme 2.

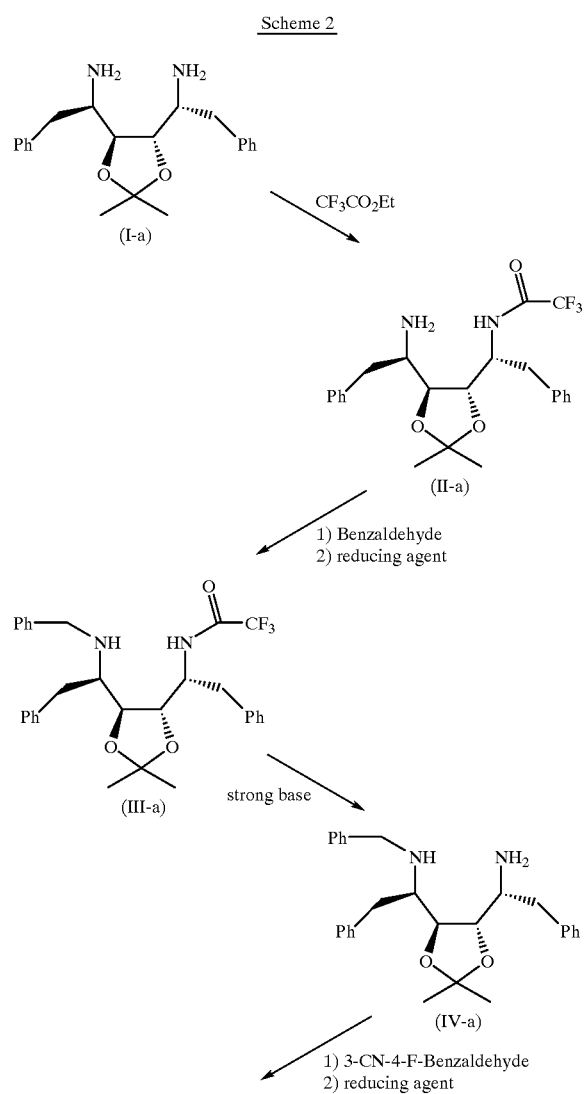

Scheme 2

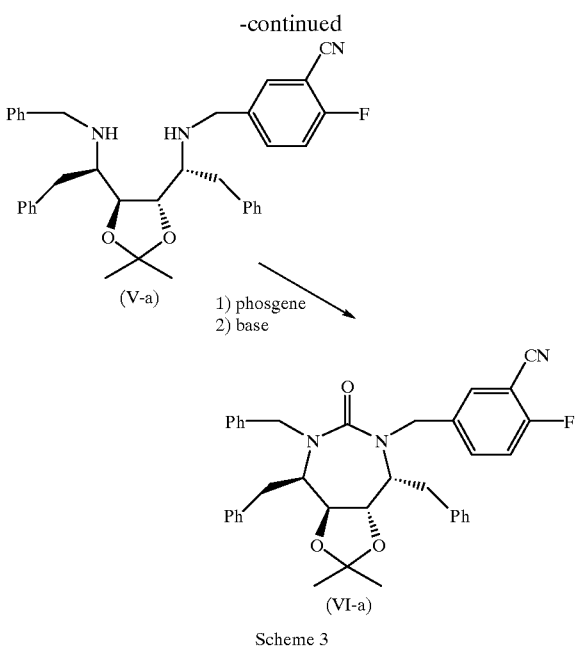

Scheme 3

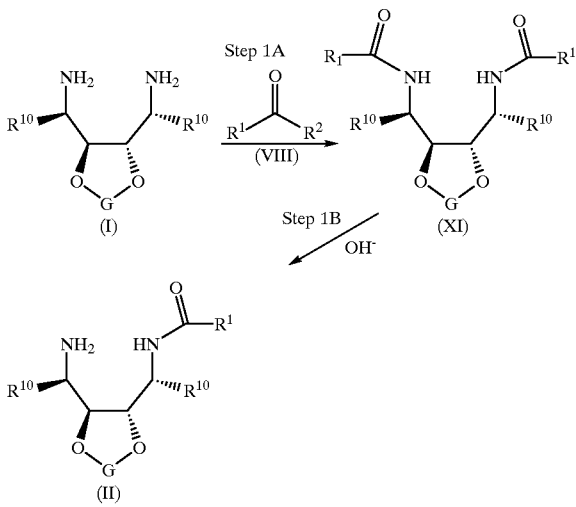

Step 1A: Bis-acylation: Preparation of a Compound of Formula (XI).

This step is conducted by reacting a diamine compound of formula (I) with an excess of a strongly electrophilic acylating agent (VIII) in the presence of a base to give a bis-acylated compound of formula (XI). By way of general guidance, to a solution of a diamine of formula (I) and about 3 equivalents base is slowly added an excess, preferably about 2 to about 5, more preferably about 2.5 equivalents of a strongly electrohphilic acylating agent while controlling the temperature. It is understood that one skilled in the art can determine the rate of addition as dependent on acylating agent and maintaining a preferred temperature of the reaction between about 0 to about 35° C. After addition of the acylating agent the reaction is aged for a sufficient amount of time, preferably about 30 minutes to about 24 hours, more preferably about 1 hour to about 3 hours, at a temperature of about 0° C. to reflux to form the bis-acylated compound (XI). The preferred temperature depends on which acylating agent is used, preferably the acylating agent is $CF_3(CO)O(CO)CF_3$ wherein the preferred temperature range is about 0 to about 35° C. The product (XI) may be separated from the reaction as a stable solid by standard methods of workup, an example of which is shown in Example 17.

It is understood that a large scope of strongly electrophilic acylating agents are suitable for this reaction, such as anhydrides, $R^1(CO)O(CO)R^1$, or $R^1$ substituted acid halides, eg. $R^1C(=O)Cl$. It is preferred that $R^1$ is a $C_1$–$C_3$ haloalkyl, such as $CF_3$, $CF_2CF_3$, $CF_2CF_2CF_3$, $CF_2Cl$, $CF_2Br$, $CCl_3$, $CBr_3$, or $CH_2F$. More preferably the acylating agent is $CF_3(CO)O(CO)CF_3$.

Preferred solvents for Step 1A include toluene, cyclohexane, hexane, heptane, methyl t-butyl ether, tetrahydrofuran, acetonitrile, water or mixtures of any of these solvents and water. Most preferably toluene.

In Step 1A, it is understood that a wide range of bases are suitable. Preferred bases include trialkylamines, pyridine, and inorganic bases; more preferably triethylamine, pyridine, sodium hydroxide, or potassium carbonate; most preferably triethylamine.

Step 1B: Mono-deacylation: Preparation of a Compound of Formula (II).

This step is conducted by reacting a diacyl diamine of formula (XI) with a suitable base to form a compound of formula (II). By way of general guidance, a diacyl diamine of formula (XI) is reacted with about 1 to 3, preferably about 1 to 2, more preferably about 1.0 to about 1.2 equivalents of a suitable base in a suitable solvent at a suitable temperature for a sufficient amount of time and subsequently quenched with about 1.0 to about 1.2 equivalents of a quenching acid, preferably acetic acid, to form the monoacylated derivative (II). Compound (II) can be used as is or can be reacted with an acid to form a suitable isolable acid addition salt. An example of workup is shown in Example 18.

Preferred acids in Step 1B for the preparation of an isolable acid addition salt include phthalic acid, salicylic acid, isophthalic acid, and malonic acid; more preferrable the acid is phthalic acid. When $R^1$ is $CF_3$ the the product is preferably isolated as the phthalate salt from a mixture of toluene and isopropanol.

A preferrable advantage to preparation of isolable acid addition salts is the further utilization of this step as a purification procedure. For example, the phthalic acid salt of (II) can be recrystallised from acetonitrile if further purification is required.

In Step 1B many suitable bases can be utilized as a suitable source of hydroxide ion such as sodium hydroxide, potassium hydroxide, lithium hydroxide, calcium hydroxide, magnesium hydroxide, potassium carbonate and water. Additional bases include a $C_1$–$C_{10}$ alkoxide salt of sodium, potassium, or lithium, in the presence of water; for example sodium methoxide and water, sodium ethoxide and water, potassium tert-butoxide and water; as well as n-butyl lithium and water. Preferably a mixture of potassium tert-butoxide and water.

A number of solvents can be used such as 2-propanol, ethanol, methanol, tetrahydrofuran, toluene, methyl t-butyl ether, cyclohexane, hexane, heptane, acetonitrile, mixtures thereof or mixtures thereof with water. More preferable is a mixture of tetrahydrofuran/methanol/water or tetrahydrofuran/methanol; most preferable is a mixture of tetrahydrofuran/methanol/water.

A suitable temperature for the mono-deacylation reaction is from about 0° C. to reflux of the solvent. The preferred temperature depends on $R^1$ and is readily determined by one skilled in the art. For example, when $R^1$ is $CF_3$ the preferred range in THF/methanol/water is about 58 to about 64° C.

It is understood that a compound of formula (II) can be synthesized from a large scope of acylating agents. It is prefered that $R^1$ in Step 1B is a $C_1$–$C_4$ haloalkyl, preferably $C_1$–$C_3$ haloalkyl, such as $CF_3$, $CF_2CF_3$, $CF_2CF_2CF_3$, $CF_2Cl$, $CF_2Br$, $CCl_3$, $CBr_3$, or $CH_2F$. More preferably $R^1$ is $CF_3$.

The following examples are meant to be illustrative of the present invention. These examples are presented to exemplify the invention and are not to be construed as limiting the inventor's scope.

Starting materials, alkylating agents and reagents of the invention can be obtained commercially or prepared in a number of ways well known to one skilled in the art of organic synthesis. The starting materials and alkylating agents of the invention can be synthesized using the methods described in U.S. Pat. No. 5,532,356, U.S. Pat. No. 5,610,294, U.S. Pat. No. 5,530,124, U.S. Pat. No. 5,532,357, U.S. Pat. No. 5,559,252, and U.S. Pat. No. 5,637,780, the disclosures of which are hereby incorporated by reference. Where the above references describe alkylating agents that are benzyl halides or alkyl halides or the like, it is understood that one skilled in the art of organic synthesis can readily oxidize the halide to an aldehyde by methods known in the art.

As described herein, HPLC conditions for the determination of starting materials, products and intermediates in Step (1) are: Column: Waters Symmetry-C18, 150×3.9 mm, 5 μm; flow rate: 1.5 ml/minute; injection volume: 5 microliters; wavelength: 220 nm; Oven temperature: 40° C.; Solvent A: 5 mM sodium dihydrogen phosphate and 5 mM diammonium hydrogen phosphate in water; Solvent B: acetonitrile; gradient timetable for solvents: T=0 minutes 65:35 A:B; T=12 minutes 30:70 A:B; T=15 minutes 15:85 A:B.

EXAMPLE 1

Monoacylation of Substituted 1,4 diaminobutane wherein the acylating agent is Methyl trifluoroacetate; $R^2$=OMe.

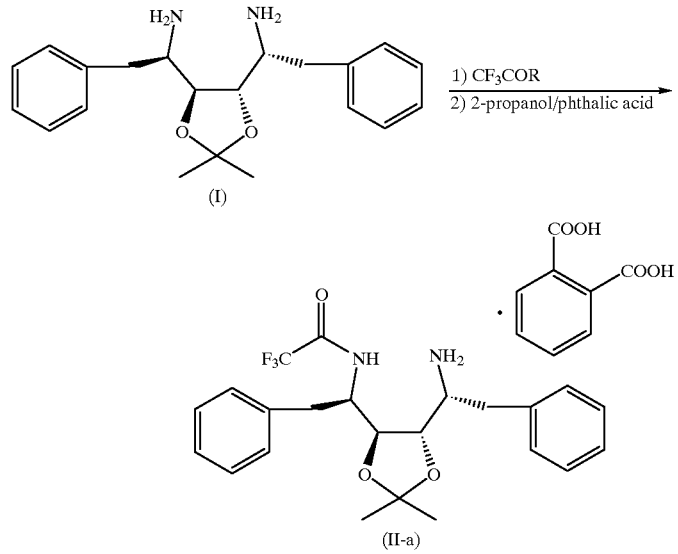

To a stirred solution of (I) (14.63 g, 43.03 mmole) in toluene (100 ml) under nitrogen at 25° C. was added methyl trifluoroacetate (6.06 ml, 7.71 g, 60.24 mmole, 1.4 eq) and stirred at 25° C. for 1.5 hr. Upon completion of the reaction, as determined by HPLC, the excess methyl trifluoroacetate was removed via vacuum distillation. To the reaction mixture was added 2-propanol (43 ml) followed by phthalic acid (6.79 g, 40.88 mmole, 0.95 eq) in five equal portions over 1 hr. The resulting slurry was stirred at 50° C. for 1 hr, cooled to 20° C., stirred for 2 hrs and filtered. The product was dried to a constant weight in vacuo to give 21.74 g (84%) of (II-a).

EXAMPLE 2

Monoacylation of Substituted 1,4 diaminobutane, as in Example 1, wherein the acylating agent is Ethyl trifluoroacetate, $R^2$=OEt.

To a stirred solution of (I) (1.03 Kg, 3.03 moles) in toluene (7.00 liters) under nitrogen at 25° C. was added ethyl trifluoroacetate (0.506 liters, 0.604 Kg, 4.24 moles, 1.4 eq). The reaction was warmed to 45° C. and stirred for 4 hrs. Upon completion of the reaction, as determined by HPLC, the excess ethyl trifluoroacetate was removed via vacuum distillation. The reaction mixture was cooled to 25° C. and 2-propanol (3.10 liters) was added followed by phthalic acid (0.48 Kg, 2.88 moles, 0.95 eq) in five equal portions over 1 hr. The resulting slurry was stirred at 50° C. for 1 hr, cooled to 20° C., stirred for 2 hrs and filtered. The product was dried to a constant weight in vacuo to give 1.65 Kg (90%) of (II-a).

EXAMPLE 3

Monoacylation of Substituted 1,4 diaminobutane, as in Example 1, wherein the acylating agent is Isopropyl trifluoroacetate, $R^6$=O-isopropyl.

To a stirred solution of (I) (5.21 g, 15.33 mmole) in toluene (35 ml) under nitrogen at 25° C. was added isopropyl trifluoroacetate (4.10 ml, 4.55 g, 29.13 mmole, 1.9 eq) and stirred at 55° C. for 24 hr. Upon completion of the reaction, as determined by HPLC, 2-propanol (15 ml) was added followed by phthalic acid (2.32 g, 14.56 mmole, 0.95 eq) in five equal portions over 1 hr. The resulting slurry was stirred at 50° C. for 1 hr, cooled to 20° C., stirred for 2 hrs and filtered. The product was dried to a constant weight in vacuo to give 8.04 g (87%) of (II-a).

EXAMPLE 4

Monoacylation of Substituted 1,4 diaminobutane, as in Example 1, wherein the acylating agent is Ally trifluoroacetate, $R^2$=O-allyl.

To a stirred solution of (I) (5.21 g, 15.33 mmole) in toluene (35 ml) under nitrogen at 25° C. was added ally trifluoroacetate (2.68 ml, 3.17 g, 20.57 mmole, 1.34 eq) and stirred at 25° C. for 2 hr. Upon completion of the reaction, as determined by HPLC, 2-propanol (15 ml) was added followed by phthalic acid (2.32 g, 14.56 mmole, 0.95 eq) in five equal portions over 1 hr. The resulting slurry was stirred at 50° C. for 1 hr, cooled to 20° C., stirred for 2 hrs and filtered. The product was dried to a constant weight in vacuo to give 8.30 g (90%) of (II-a).

EXAMPLE 5

Monoacylation of Substituted 1,4 diaminobutane, as in Example 1, wherein the acylating agent is S-ethyltrifluoro thioacetate, $R^2$=thio ethyl.

To a stirred solution of (I) (5.21 g, 15.33 mmole) in toluene (35 ml) under nitrogen at 0° C. was added S-ethyltrifluoro thioacetate (2.63 ml, 3.25 g, 20.57 mmole, 1.34 eq) and warmed to 25° C. over 1 hr. Upon completion of the reaction, as determined by HPLC, 2-propanol (15 ml) was added followed by phthalic acid (2.32 g, 14.56 mmole, 0.95 eq) in five equal portions over 1 hr. The resulting slurry was stirred at 50° C. for 1 hr, cooled to 20° C., stirred for 2 hrs and filtered. The product was dried to a constant weight in vacuo to give 8.26 g (89%) of (II-a).

EXAMPLE 6

Monoacylation of Substituted 1,4 diaminobutane, as in Example 1, wherein the acylating agent is 2,2,2-Trifluoroethyl trifluoroacetate, $R^2$=2,2,2-Trifluoro ethoxy.

To a stirred solution of (I) (5.21 g, 15.33 mmole) in toluene (35 ml) under nitrogen at 0° C. was added 2,2,2-Trifluroethyl trifluoroacetate (2.36 ml, 3.46 g, 17.64 mmole, 1.15 eq). Upon completion of the reaction, as determined by HPLC, 2-propanol (15 ml) was added, the reaction was warmed to 25° C. and phthalic acid (2.32 g, 14.56 mmole, 0.95 eq) was added in five equal portions over 1 hr. The resulting slurry was stirred at 50° C. for 1 hr, cooled to 20° C., stirred for 2 hrs and filtered. The product was dried to a constant weight in vacuo to give 8.26 g (89%) of (II-a).

EXAMPLE 7

Monoacylation of Substituted 1,4 diaminobutane, as in Example 1, wherein the acylating agent is Phenyl trifluoroacetate, $R^2$=OPh.

To a stirred solution of (I) (5.21 g, 15.33 mmole) in toluene (35 ml) under nitrogen at 0° C. was added phenyl trifluoroacetate (2.63 ml, 3.35 g, 17.64 mmole, 1.15 eq) and warmed to 25° C. over 1 hr. Upon completion of the reaction, as determined by HPLC, 2-propanol (15 ml) was added followed by phthalic acid (2.32 g, 14.56 mmole, 0.95 eq) in five equal portions over 1 hr. The resulting slurry was stirred at 50° C. for 1 hr, cooled to 20° C., stirred for 2 hrs and filtered. The product was dried to a constant weight in vacuo to give 8.33 g (90%) of (II-a).

EXAMPLE 8

Monoacylation of Substituted 1,4 diaminobutane, as in Example 1, wherein the acylating agent is 4-nitro phenyl trifluoroacetate, $R^2$=Op-$NO_2$Ph.

To a stirred solution of (I) (5.21 g, 15.33 mmole) in toluene (35 ml) under nitrogen at 0° C. was added phenyl trifluoroacetate (4.15 g, 17.64 mmole, 1.15 eq) and warmed to 25° C. over 1 hr. Upon completion of the reaction, as determined by HPLC, 2-propanol (15 ml) was added followed by phthalic acid (2.32 g, 14.56 mmole, 0.95 eq) in five equal portions over 1 hr. The resulting slurry was stirred at 50° C. for 1 hr, cooled to 20° C., stirred for 2 hrs and filtered. The product was dried to a constant weight in vacuo to give 8.46 g (92%) of (II-a).

EXAMPLE 9

Monoacylation of Substituted 1,4 diaminobutane, as in Example 1, wherein the acylating agent is 2-(Trifluroacetoxy) pyridine, $R^{20}$=2-hydroxy pyridine.

To a stirred solution of (I) (5.00 g, 14.70 mmole) in toluene (35 ml) under nitrogen at 0° C. was added 2-(trifluroacetoxy) pyridine (2.80 g, 2.07 ml, 14.70 mmole, 1.0 eq. Upon completion of the reaction, as determined by HPLC, the solvent was removed under reduced pressure and the yield of the mono trifluoro acetyl derivative determined by nmr to be 10%.

EXAMPLE 10

Monoacylation of Substituted 1,4 diaminobutane wherein the acylating agent is Ethyl pentafluoropropionate, $R^1$=$CF_2CF_3$.

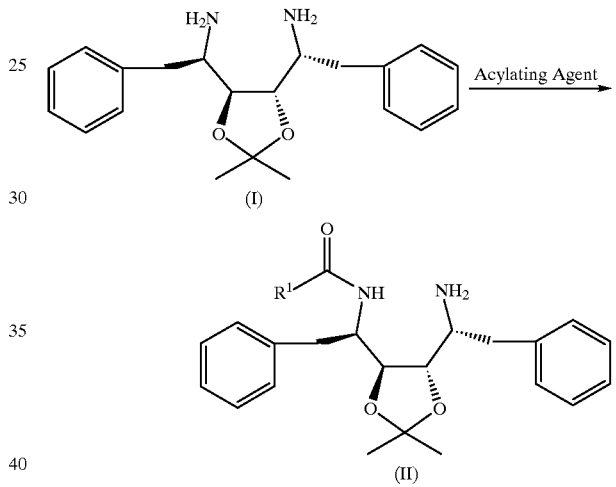

To a stirred solution of (I) (10.40 g, 30.66 mmole) in toluene (70 ml) under nitrogen at 25° C. was added ethyl pentafluoropropionate (11.18 g, 8.61 ml, 58.25 mmole, 1.9 eq) and the reaction warmed to 60° C. Upon completion of the reaction, as determined by HPLC, the solvent was removed under reduced pressure to give the mono pentafluoro amide product in 79% yield.

EXAMPLE 11

Monoacylation of Substituted 1,4 diaminobutane, as in Example 10, wherein the acylating agent is Ethyl heptafluorobutyrate, $R^1$=$CF_2CF_2CF_3$.

To a stirred solution of (I) (5.00 g, 14.70 mmole) in toluene (35 ml) under nitrogen at 25° C. was added ethyl heptafluorobutyrate (6.76 g, 4.84 ml, 27.93 mmole, 1.9 eq) and stirred at 60° C. for 2.5 days. Upon completion of the reaction, as determined by HPLC, the solvent was removed under reduced pressure to give the mono heptafluoro amide product in 79% yield.

EXAMPLE 12

Monoacylation of Substituted 1,4 diaminobutane, as in Example 10, wherein the acylating agent is Ethyl bromofluoroacetate, $R^1$=$CF_2Br$.

To a stirred solution of (I) (5.00 g, 14.70 mmole) in toluene (35 ml) under nitrogen at 25° C. was added ethyl bromofluoroacetate (4.17 g, 2.64 ml, 20.58 mmole, 1.4 eq) and stirred at 25° C. overnight. Upon completion of the reaction, as determined by HPLC, the solvent was removed under reduced pressure to give the bromo difluoro amide product in 82% yield.

EXAMPLE 13

Monoacylation of Substituted 1,4 diaminobutane, as in Example 10, wherein the acylating agent is Methyl-2-chloro-2,2-difluoroacetate, $R^2=CF_2Cl$.

To a stirred solution of (I) (5.21 g, 15.33 mmole) in toluene (35 ml) under nitrogen at 25° C. was added methyl-2-chloro-2,2-difluoroacetate (2.49 g, 1.86 ml, 17.63 mmole, 1.15 eq) and stirred at 25° C. for 5 hrs. Upon completion of the reaction, as determined by HPLC, the solvent was removed under reduced pressure to give the chloro difluoro amide product in 86% yield.

EXAMPLE 14

Monoacylation of Substituted 1,4 diaminobutane, as in Example 10, wherein the acylating agent is Ethyl trichloroacetate, $R^1=CCl_3$.

To a stirred solution of (I) (5.00 g, 14.70 mmole) in toluene (35 ml) under nitrogen at 25° C. was added ethyl trichloroacetate (5.33 g, 3.88 ml, 27.93 mmole, 1.9 eq) and stirred at reflux for 3 days. Upon completion of the reaction, as determined by HPLC, the solvent was removed under reduced pressure to give the trichloro amide product in 63% yield.

EXAMPLE 15

Monoacylation of Substituted 1,4 diaminobutane, as in Example 10, wherein the acylating agent is Ethyl tribromoacetate, $R^1=CBr_3$.

To a stirred solution of (I) (5.00 g, 14.70 mmole) in toluene (35 ml) under nitrogen at 25° C. was added ethyl tribromoacetate (6.39 g, 2.74 ml, 20.58 mmole, 1.4 eq) and stirred at 45° C. for 3 days. Upon completion of the reaction, as determined by HPLC, the solvent was removed under reduced pressure to give the tribromo amide product in 80% yield.

EXAMPLE 16

Monoacylation of Substituted 1,4 diaminobutane, as in Example 10, wherein the acylating agent is Ethyl fluoroacetate, $R^2=CH_2F$.

To a stirred solution of (I) (5.00 g, 14.70 mmole) in toluene (35 ml) under nitrogen at 25° C. was added ethyl fluoroacetate (2.18 g, 1.99 ml, 20.58 mmole, 1.4 eq) and stirred at reflux for 7 days. Upon completion of the reaction, as determined by HPLC, the solvent was removed under reduced pressure to give the monofluoro amide product in 33% yield.

EXAMPLE 17

Bis-acylation: Preparation of a Compound of Formula (XI) wherein $R^1=CF_3$.

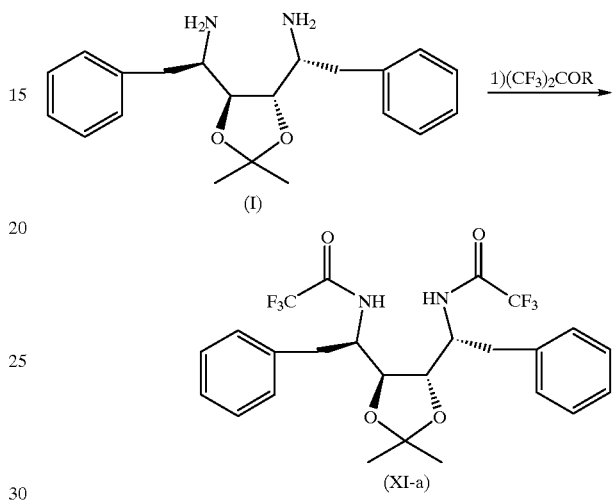

To a stirred solution of (I) (53.3 g, 157 mmole), toluene (113 ml) and triethylamine (65 ml, 470 mmole, 3 eq) under nitrogen was slowly added trifluoroacetic anhydride (55 ml, 391 mmole, 2.5 eq) over 0.75 h at 0 to 35° C. The reaction mass was aged for 1 h at about 25° C. To the reaction mixture was added water (250 ml) and ethyl acetate (250 ml) and the layers were separated, discarded aqueous phase. The organic phase was washed with 5% aqueous sodium bicarbonate (250 ml). The reaction mass was concentrated in vacuo to 102 g of an oily solid. Toluene (170 ml) was added and the resulting slurry heated to 70° C. to dissolve. Cyclohexane (350 ml) was slowly added at about 70° C. The resulting slurry was allowed to cool slowly to about 20° C., stirred for 3.5 days, filtered and washed with cyclohexane (3×50 ml). The product was dried to a constant weight in vacuo to give 42.0 g (50%) of (XI-a).

EXAMPLE 18

Mono-deacylation, Step 1B: Preparation of a Compound of Formula (II) wherein $R^1=CF_3$.

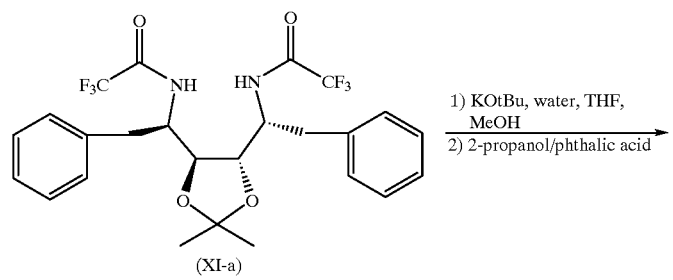

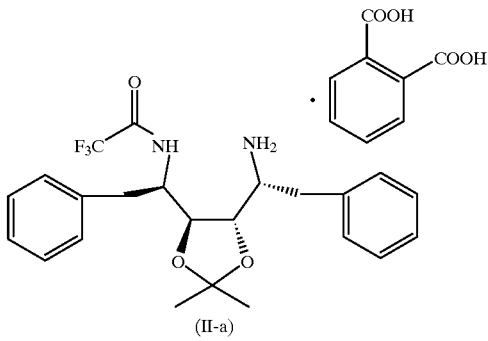

(II-a)

To a stirred solution of (XI-a) (106.5 g, 0.20 mole) in tetrahydrofuran (500 ml) under nitrogen at about 25° C. was added a solution of potassium tert-butoxide in tetrahydrofuran (1.0 M, 220 ml, 0.22 mole, 1.1 eq), water (4 ml, 0.22 mole, 1.1 eq) and methanol (250 ml). The reaction mass was heated to about 60° C. and aged for 18 hr. The reaction mass was cooled to about 20° C. and acetic acid (13.7 ml, 0.24 moles, 1.2 eq) was added. The reaction mass was distilled under vacuum to about 300 ml total volume. Toluene (700 ml) was added and the distillation continued to about 400 ml final volume. Toluene (100 ml), water (400 ml) and potassium carbonate (25 g) were added to about pH 10. The layers were separated, and the aqueous phase discarded. The organic phase was washed with 10% aqueous sodium chloride (500 ml), then vacuum distilled to about 400 ml final volume. Toluene (100 ml) and 2-propanol (220 ml) were added and the reaction mass was heated to 45° C. Phthalic acid (31.6 g, 0.19 mole, 0.95 eq) was added in five equal portions over 30 mins. The resulting slurry was stirred at about 50° C. for 1 hr, cooled to 20° C., stirred for 2 hrs, filtered and washed with toluene (3×100 ml). The product was dried to a constant weight in vacuo to give 109.1 g (91%) of (II-a).

EXAMPLE 19

Reductive Amination: Preparation of a Compound of Formula (III-a) using a Chemical Reducing agent.

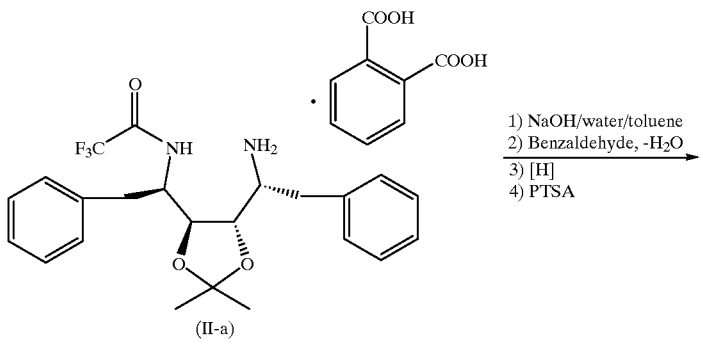

(II-a)

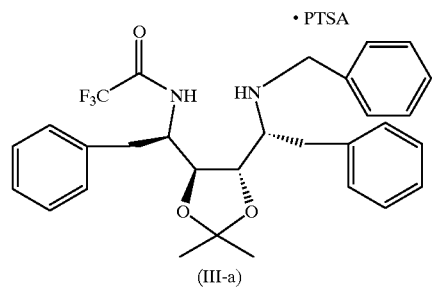

(III-a)

To a 22 L round bottom flask was added toluene (4.30 liters), (II-a) (1.20 Kg, 1.99 moles), water (4.30 liters) and 50% sodium hydroxide solution (335 g, 4.18 moles, 2.1 eq.). The mixture was stirred vigorously for 30 mins., agitation stopped, and the aqueous phase discarded. To the organic phase was added toluene (4.30 liters) and the solution was heated to reflux, distilling to a Dean and Stark trap until no more water was evolved, then cooled to 80° C. The Dean and Stark trap was drained, benzaldehyde (211 g, 203 ml, 1.99 moles) added to the reaction, and the reaction mixture heated to reflux, distilling to the Dean and Stark trap until no more water was evolved. The reaction mixture was cooled to 25° C., acetic acid (145 g, 135 ml, 2.34 moles, 1.2 eq.) and sodium triacetoxy borohydride (633 g, 2.99 moles, 1.5 eq.) were added. The reaction mixture was stirred overnight at 25° C. Water (2.15 liters) was slowly added, the pH of the aqueous phase was adjusted to 7–8 by the addition of 50% sodium hydroxide and the aqueous phase then discarded. The solvent was removed via vacuum distillation to give an oil which was dissolved in cyclohexane (9.75 liters). A solution of para-toluene sulphonic acid (378 g, 1.99 moles)

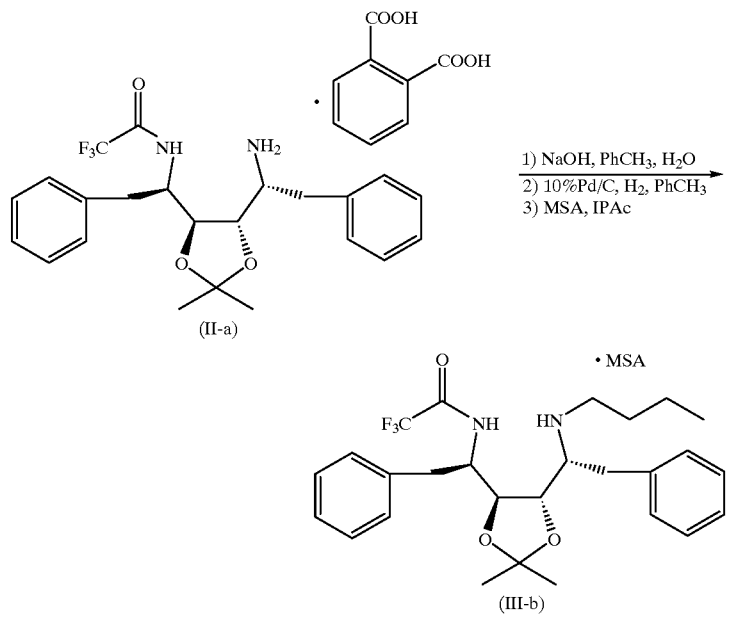

in 2-propanol (4.20 liters) was added in five equal portions over 1 hour. The resulting slurry was heated at reflux for 20 mins., cooled to 10° C. and filtered. The product was dried to a constant weight in vacuo to give 1.25 Kg (90%) of (III-a).

EXAMPLE 19a

Reductive Amination: Preparation of a Compound of Formula (III-a) using a Hydrogenation metal catalyst.

To a 5 L round bottom flask was added toluene (3.00 liters), (II-a) (0.468 Kg, 0.77 moles), water (1.30 liters) and 50% sodium hydroxide solution (0.13 g, 1.62 moles, 2.1 eq.). The mixture was stirred vigorously for 30 mins., agitation stopped, and the aqueous phase discarded. The solution was heated to reflux, distilling to a Dean and Stark trap until no more water was evolved, then cooled to 80° C. The Dean-Stark trap was drained, benzaldehyde (82 g, 79 ml, 0.77 moles) added to the reaction, and the reaction mixture heated to reflux, distilling to the Dean and Stark trap until no more water was evolved. The Dean-Stark trap was replaced with a distillation apparatus and 2.5 liters of toluene was distilled. The solution was cooled to 55° C., methanol (1.7 liters) was added and 1.7 liters of solvent was distilled. The solution was cooled to 30° C. and methanol (2.5 liters) was added. The imine was hydrogenated over 5% Pt/C at 25° C. at 40 psi. Once the reaction was complete, as determined by hydrogen uptake, the reaction mixture was filtered through celite and the methanol removed via vacuum distillation. The crude product was dissolved in cyclohexane (1.5 liters) and 2-propanol (1.5 liters) and para-toluene sulphonic acid (80 g, 0.77 moles) was added portion wise. The resulting slurry was heated to reflux, cooled to 5° C. and filtered. The product was dried to a constant weight in vacuo to give 458 g (85%) of (III-a).

EXAMPLE 19b

Reductive Amination: Preparation of a Compound of Formula (III-b) using a Hydrogenation metal catalyst.

To a slurry of (II-a) (100 g, 0.166 moles) in toluene (400 ml) was added water (200 ml) and 10N sodium hydroxide solution (36.4 ml, 0.364 mol, 1.2 eq). The mixture was stirred for 30 mins, the agitation stopped and the phases separated. The aqueous layer was washed with toluene (200 ml) and the combined organic layers were washed with water (200 ml), clarified through a Celite bed, and concentrated to a residual volume of 600 mL by vacuum distillation, then diluted with toluene (200 ml) to a final volume of 800 ml. To the solution was added 10% palladium on carbon (15 g, 50% water content), triethylamine (1.0 g, 0.01 moles, 0.06 eq.), and butyraldehyde (14.6 g 0.202 moles, 1.2 eq.). After evacuating and purging with hydrogen (3×), the mixture was hydrogenated for a period of 24 hrs under 1 psi of hydrogen pressure. After completion of the reaction, as determined by HPLC, the catalyst was removed by filtration, washed with toluene (100 ml), and the filtrate concentrated to 200 ml by vacuum distillation. Isopropyl acetate (500 ml) was added and the solution warmed to 25–28° C. A solution of methanesulfonic acid (16.2 g, 0.168 moles) in isopropyl acetate (140 ml) was added slowly over a period of 20 minutes as the temperature increased to 34–36° C. The resulting slurry was cooled to 25° C. and stirred for 1 hour. The product was filtered, washed with isopropyl acetate (100 ml) and dried to a constant weight in vacuo to give 83 g (85%) of (III-b).

EXAMPLE 20

Combined Deacylation, Step 3, and Reductive Amination, Step 4: Preparation of a Compound of Formula (V-a).

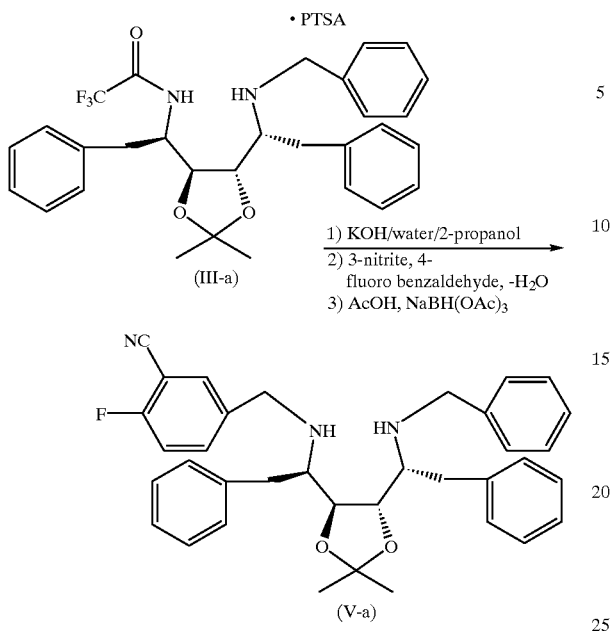

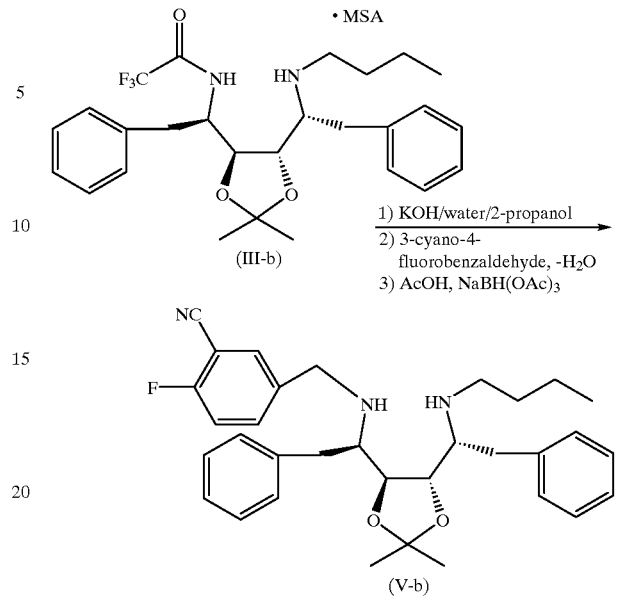

A mixture of (III-a) (1.20 Kg, 1.72 moles), 2-propanol (3.25 liters) and a solution of potassium hydroxide (385 g, 6.86 moles, 4.0 eq.) in water (2.60 liters) was heated at reflux for 60 mins. The reaction was cooled to 25–30° C., and the 2-propanol removed via vacuum distillation until the volume was reduced by approximately half. Toluene (2.50 liters) was added, the phases separated and the aqueous phase discarded. Toluene (5.00 liters) was added and the solution was distilled at atmospheric pressure until the temperature of the distillate was ≧110° C. The solution was cooled to 80° C., 3-nitrile, 4-fluoro benzaldehyde (256 g, 1.72 moles, 1 eq.) was added and the reaction mixture was heated to reflux, distilling to a Dean and Stark trap until no more water was evolved. The reaction mixture was cooled to 25° C., acetic acid (124 g, 118 ml, 2.06 moles, 1.2 eq.) and sodium triacetoxy borohydride (546 g, 2.57 moles, 1.5 eq.) were added. The reaction mixture was stirred overnight at 25° C. Water (1.85 liters) was slowly added, the pH of the aqueous phase was adjusted to 7–8 by the addition of 50% sodium hydroxide and the aqueous phase then discarded. The solvent was removed via vacuum distillation to a final volume of 1.5–2.0 liters. Heptane (7.75 liters) was added, the resulting slurry was heated to reflux, cooled to 10° C. and filtered. The product was dried to a constant weight in vacuo to give 866 g (90%) of (V-a).

A mixture of (III-b) (0.70 Kg, 1.2 moles), 2-propanol (1.4 liters), potassium hydroxide (0.30 kg, 4.5 moles, 3.8 eq.) and water (0.44 liters) was distilled to 83° C. pot temperature. The reaction mass was cooled to about 70° C., and toluene (1.4 liters) and water (1.4 liters) were added. The pH of the mixture was adjusted by adding acetic acid to pH≦9 and then adding sodium carbonate to pH≧10. The reaction mass was distilled at atmospheric pressure until the pot temperature was ≦103° C. The solution was cooled to about 25° C., toluene (1.4 liters) was added and the layers were separated, discarding the aqueous phase. The organic phase was washed with water (1.4 liters). The solution was distilled at atmospheric pressure until the temperature of the distillate was ≧110° C. The solution was cooled to 35° C., 3-cyano-4-fluorobenzaldehyde (0.19 kg, 1.2 moles, 1 eq.) and toluene (0.7 liters) were added. The solution was distilled at atmospheric pressure until the temperature of the distillate was ≧110° C. The reaction mixture was cooled to about 25° C., acetic acid (0.08 liter, 1.43 moles, 1.2 eq.) and sodium triacetoxy borohydride (0.45 kg, 2.14 moles, 1.8 eq.) were added. The reaction mixture was stirred overnight at about 25° C. A solution of sodium carbonate (0.13 kg, 1.2 moles, 1 eq) in water (1.4 liters) was slowly added, the layers separated and the aqueous phase discarded. The organic phase was washed with water (1.4 liters). The reaction mass was concentrated via distillation to provide (V-b) as a solution in toluene. This solution was used as is in the next step assuming a quantitative yield of (V-b) from (III-b).

EXAMPLE 20a

Combined Deacylation; Step 3, and Reductive Amination, Step 4: Preparation of a Compound of Formula (V-b).

EXAMPLE 22

Cyclization; Step 5: Preparation of a Compound of Formula (VII-a) via the intermediate (VI-a)

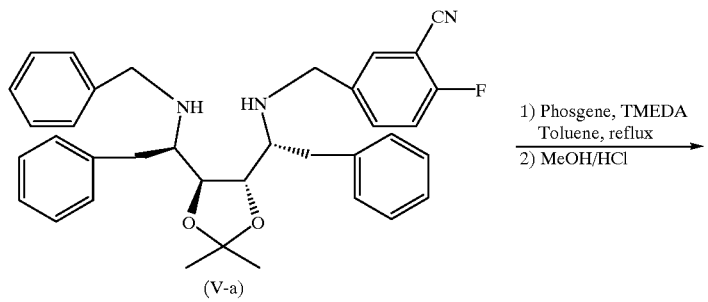

(V-a)

1) Phosgene, TMEDA
   Toluene, reflux
2) MeOH/HCl

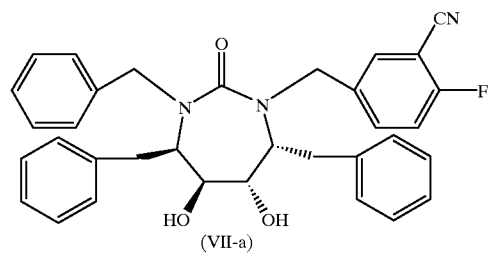

(VII-a)

To a solution of (V-a) (210 g, 0.3725 moles) and N,N,N',N'-tetramethylethylenediamine (78 g, 104 ml, 0.67 moles, 1.8 eq) in toluene (1260 ml) at reflux was added a solution of phosgene in toluene (0.15 M, 4470 ml, 0.67 moles, 1.8 eq) subsurface over 5–6 hours. During the addition of the phosgene solution, toluene was distilled off such that the maximum the volume of the reaction mixture was not allowed to exceed 3150 ml's. The reaction was cooled to 10° C. and then filtered to remove TMEDA•HCl salt. Toluene was removed via vacuum distillation until the final volume was 1000 ml. The reaction mixture was cooled to 40° C., methanol (210 ml) and concentrated hydrochloric acid (420 mL) were added, stirred at 55–65° C. for 1 hour, then cooled to 50° C. The phases were separated and the aqueous phase was discarded. The organic phase was washed with water that was preheated to 50° C. (210 ml), the phases were separated and the aqueous phase discarded. To the organic phase was added water (840 ml) and the resulting slurry stirred for 30 minutes at 5–10° C. The entire contents were filtered and the cake washed with toluene (210 ml) and water (840 ml). The product was dried to a constant weight in vacuo to give 154 g (75%) of (VII-a).

EXAMPLE 22a

Cyclization; Step 5: Preparation of a Compound of Formula (VI-b).

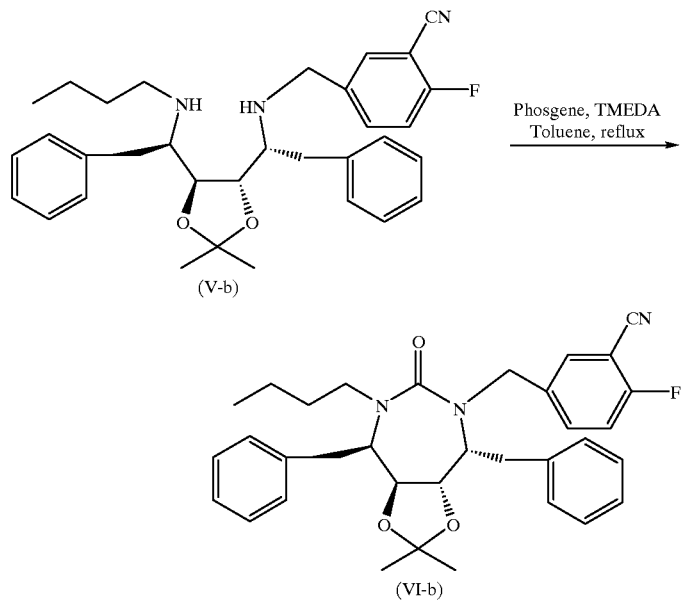

To a solution of (V-b) (296 g, 0.559 moles) and N,N,N',N'-tetramethylethylenediamine (117 g, 152 ml, 1.00 moles, 1.8 eq) in toluene (1940 ml) at reflux was added a solution of phosgene in toluene (0.15 M, 6670 ml, 1.8 eq) subsurface over 5–6 hours. During the addition of the phosgene solution, toluene was distilled off such that the maximum the volume of the reaction mixture was not allowed to exceed 4900 ml's. The reaction was cooled to 20° C., silica gel (78 g) was added and the reaction mixture stirred for 30 mins at 20° C., then filtered. The reaction mixture was washed with water (3×1500 ml) and the aqueous phases discarded. The solvent was removed in vacuo to give an oil which was dissolved in a mixture of amylacetate (89 ml) and heptane (4760 ml). (VI-b) slowly crystalised and the resulting slurry was stirred at 10–20° C. for 4–8 hrs, then filtered. The product was dried to a constant weight in vacuo to give 233 g (75%) of (VI-b).

EXAMPLE 23

Synthesis of Compound of Formula (X-b).

liters). The reaction mixture was stirred at room temperature until the reaction was complete as determined by HPLC (<0.1 A % acetonide remaining). A 30% solution of sodium chloride (1.4 liters) was added and the mixture stirred for 10 minutes, the phases separated and the organic phase was washed with 2M hydrochloric acid (2.1 liters) and 10% aqueous potassium bicarbonate solution (1.4 liters). The organic phase was distilled to a head temperature of 75° C., additional ethyl acetate was added as required such that the volume did not fall below 2.0 liters. The solution was cooled to 50° C. and methanesulphonic acid (33 ml, 0.50 moles, 1.0 eq), ethanol (0.20 liters) and benzoyltrifluoroacetone (11.5 g, 0.1 eq) were added and the reaction mixture was heated at 65° C. for 2 hours. The solution was cooled to 20° C. and washed with a 10% aqueous solution of potassium bicarbonate (1.4 liters). The organic phase was distilled to a head

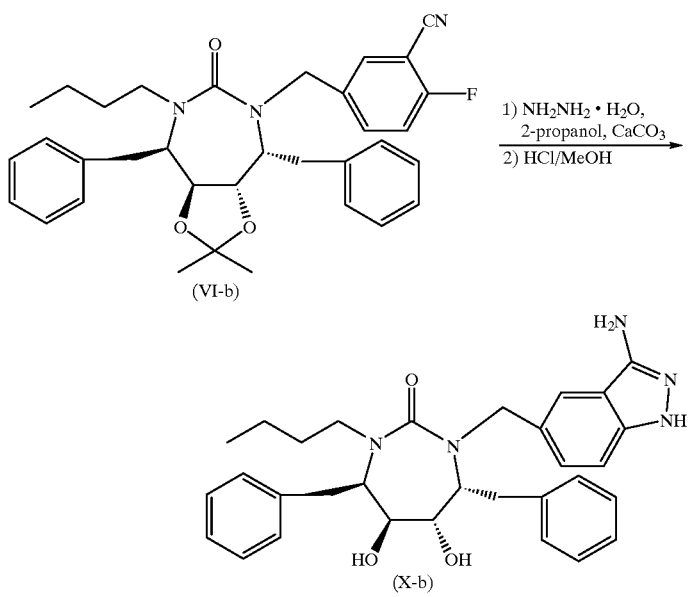

A mixture of (VI-b) (0.28 Kg, 0.50 moles), 2-propanol (0.56 liters), hydrazine monohydrate (0.24 liters) and calcium carbonate (32 g) was heated at reflux under nitrogen for 6 hours. The reaction was checked for completion by HPLC (criteria for completion <0.3 area % (VI-b) remaining). The reaction was cooled to room temperature, ethyl acetate (1.8 liters) was added and the reaction mixture stirred for 10 minutes. The inorganic salts were filtered off and washed with ethyl acetate (0.2 liters). The combined organic filtrates were washed with 2M hydrochloric acid (2.1 liters). Methanol was added to the organic phase followed by the slow addition of of 2M hydrochloric acid (1.2 temperature of 75° C., additional ethyl acetate was added as required such that the volume did not fall below 2.0 liters. The solution was cooled to 20° C. and seeded. The resulting slurry was cooled to 5° C. and stirred for one hour, filtered and washed with ethyl acetate until the yellow colour was removed. The product was dried in vacuo to give 224 g (85%) of (X-b).

EXAMPLE 23a

Synthesis of Compound of Formula (X-a).

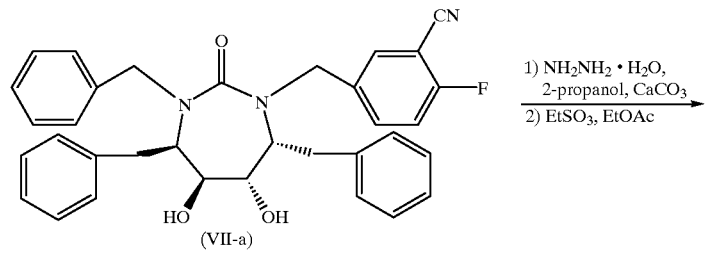

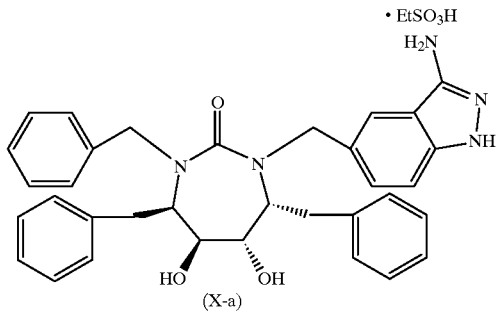

(X-a)

A mixture of (VII-a) (0.56 Kg, 1.00 moles), 2-propanol (1.1 liters), hydrazine monohydrate (0.50 liters) and calcium carbonate (62 g) was heated at reflux under nitrogen for 6 hours. The reaction was checked for completion by HPLC (criteria for completion <0.3 area % (VII-a) remaining). The reaction was cooled to room temperature, ethyl acetate (4.0 liters) was added and the reaction mixture stirred for 10 minutes. The inorganic salts were filtered off and washed with ethyl acetate (1.6 liters). The combined organic filtrates were washed twice with 2M hydrochloric acid (4.2 liters) and once with a 10% aqueous solution of potassium bicarbonate (2.8 liters). The organic phase was distilled to a head temperature of 75° C., additional ethyl acetate was added as required such that the volume did not fall below 5.6 liters. The solution was cooled to 50° C. and ethanesulphonic acid (112 g, 1.02 moles, 1.02 eq), ethanol (0.65 liters) and benzoyltrifluoroacetone (22.4 g, 0.1 eq) were added. The solution was heated at 60° C. for 2 hours then cooled to 35° C. and seeded, cooled to 20° C., stirred for one hour then filtered. The wet cake was washed with ethyl acetate until the yellow colour was removed. The product was dried in vacuo to give 571 g (85%) of (X-a).

What is claimed is:

1. A process for the preparation of a compound of formula (VI):

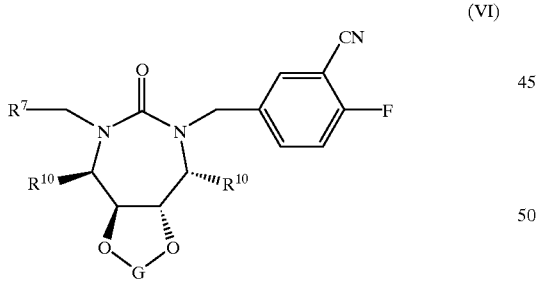

(VI)

wherein:

$R^7$ is selected from the following:
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$; and
a $C_3$–$C_{14}$ carbocyclic ring system substituted with 0–3 $R^{11}$;

$R^{10}$ is $C_1$–$C_{10}$ alkyl, benzyl, naphthylmethyl, 3,4-methylenedioxybenzyl, or $C_1$–$C_4$ alkyl substituted with phenyl wherein said phenyl is substituted with 0–3 $R^{10a}$;

$R^{10a}$ is $C_1$–$C_4$ alkyl, $C_1$–$C_4$ alkoxy, halo or cyano;

$R^{11}$ is selected from one or more of the following:
$C_1$–$C_4$ alkoxy, $C_1$–$C_4$ alkyl, $C_2$–$C_6$ alkoxyalkyl, benzyl, phenethyl, phenoxy, benzyloxy, methylenedioxy, ethylenedioxy, $C_2$–$C_4$ alkenyl, $C_3$–$C_{10}$ cycloalkyl, $C_3$–$C_6$ cycloalkylmethyl, $C_3$–$C_6$ cycloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy;
—C(=O)$R^{13}$, oxo, cyano, nitro, —CH$_2$NR$^{13}$R$^{14}$, —NR$^{13}$R$^{14}$, —CO$_2$R$^{13}$, —OC(=O)R$^{13}$, —OR$^{13}$, —OCH$_2$CO$_2$R$^{13}$, —S(O)$_2$R$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$;
$C_1$–$C_4$ alkyl substituted with —NR$^{13}$R$^{14}$; and
$C_3$–$C_{14}$ carbocyclic residue substituted with 0–3 $R^{16}$;

$R^{13}$ is independently selected from:
$C_1$–$C_6$ alkyl substituted with 0–3 $R^{15}$;
$C_2$–$C_6$ alkenyl substituted with 0–3 $R^{15}$; and
phenyl substituted with 0–3 $R^{16}$;

$R^{14}$ is independently selected from:
$C_1$–$C_6$ alkoxy, $C_2$–$C_6$ alkenyl, phenyl, benzyl, and $C_1$–$C_6$ alkyl substituted with 0–3 $C_1$–$C_4$ alkoxy; or $R^{13}$ and $R^{14}$ can alternatively join to form —(CH$_2$)$_4$—, —(CH$_2$)$_5$—, —CH$_2$CH$_2$N(CH$_3$)CH$_2$CH$_2$—, or —CH$_2$CH$_2$OCH$_2$CH$_2$—;

$R^{15}$ is selected from one or more of the following:
$C_1$–$C_4$ alkoxy, $C_1$–$C_4$ alkyl, $C_2$–$C_6$ alkoxyalkyl, benzyl, phenethyl, phenoxy, benzyloxy, methylenedioxy, ethylenedioxy, $C_2$–$C_4$ alkenyl, $C_3$–$C_{10}$ cycloalkyl, $C_3$–$C_6$ cycloalkylmethyl, $C_3$–$C_6$ cycloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy;
—C(=O)$R^{23}$, cyano, nitro, —CH$_2$NR$^{23}$R$^{24}$, —NR$^{23}$R$^{24}$, —CO$_2$R$^{23}$ —OC(=O)R$^{23}$, —OR$^{23}$, —OCH$_2$CO$_2$R$^{23}$, —S(O)$_2$R$^{23}$, —C(=O)NR$^{23}$R$^{24}$, —NR$^{24}$C(=O)R$^{23}$, =NOR$^{24}$, —NR$^{24}$C(=O)OR$^{24}$, —OC(=O)NR$^{23}$R$^{24}$, —NR$^{23}$C(=O)NR$^{23}$R$^{24}$, —NR$^{24}$SO$_2$NR$^{23}$R$^{24}$, —NR$^{24}$SO$_2$R$^{23}$, —SO$_2$NR$^{23}$R$^{24}$;
$C_1$–$C_4$ alkyl substituted with —NR$^{23}$R$^{24}$; and
phenyl substituted with 0–3 $R^{16}$;

$R^{16}$ is selected from one or more of the following:
H, halogen, cyano, nitro, —CH$_2$NR$^{23}$R$^{24}$, —NR$^{23}$R$^{24}$, —CO$_2$R$^{23}$, —OC(=O)R$^{23}$, —OR$^{23}$, —S(O)$_2$R$^{23}$, —C(=O)NR$^{23}$R$^{24}$, —NR$^{24}$C(=O)R$^{23}$, =NOR$^{24}$, —NR$^{24}$C(=O)OR$^{24}$, —OC(=O)NR$^{23}$R$^{24}$, —NR$^{23}$C(=O)NR$^{23}$R$^{24}$, —NR$^{24}$SO$_2$NR$^{23}$R$^{24}$, —NR$^{24}$SO$_2$R$^{23}$, —SO$_2$NR$^{23}$R$^{24}$;
$C_1$–$C_4$ alkyl, $C_2$–$C_4$ alkenyl, $C_3$–$C_6$ cycloalkylmethyl, phenyl, benzyl, phenethyl, phenoxy, benzyloxy, $C_3$–$C_6$ cycloalkoxy, methylenedioxy, ethylenedioxy, $C_1$–$C_4$ alkoxycarbonyl, pyridylcarbonyloxy, $C_1$–$C_4$ alkylcarbonyl, $C_1$–$C_4$ alkylcarbonylamino, 2-(1-morpholino)ethoxy; and $C_1$–$C_4$ alkyl substituted with —$NR^{23}R^{24}$;

$R^{23}$ is $C_1$–$C_4$ alkyl substituted with 0–3 $C_1$–$C_4$ alkoxy;

$R^{24}$ is $C_1$–$C_4$ alkyl substituted with 0–3 $C_1$–$C_4$ alkoxy; or $R^{23}$ and $R^{24}$ can alternatively join to form —$(CH_2)_4$—, —$(CH_2)_5$—, —$CH_2CH_2N(CH_3)CH_2CH_2$—, or —$CH_2CH_2OCH_2CH_2$—; and G taken together along with the oxygen atoms to which G is attached forms a group selected from:
—O—C(—$CH_2CH_2CH_2CH_2CH_2$—)—O—, —O—C($CH_2CH_3$)$_2$—O—, —O—C($CH_3$)($CH_2CH_3$)—O—, —O—C($CH_2CH_2CH_2CH_3$)$_2$—O—, —O—C($CH_3$)($CH_2CH(CH_3)CH_3$)—O—, —O—CH(phenyl)—O—, —$OCH_2O$—, —$OC(CH_3)_2O$—, and —$OC(OCH_3)(CH_2CH_2CH_3)O$—;

said process comprising:

(1) contacting a compound of formula (I):

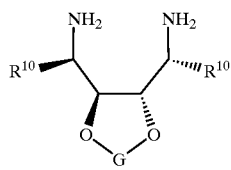

(I)

with an acylating agent of formula $R^1C(=O)R^2$;

wherein:

$R^1$ is $C_1$–$C_4$ haloalkyl;

$R^2$ is —$OR^3$, —$SR^3$, O-succinimide, or imidazolyl;

$R^3$ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;

$R^{3a}$ is selected from the group:
$C_1$–$C_4$ alkyl, $C_1$–$C_4$ alkoxy, halo, —CN, and —$NO_2$;

to form a compound of formula (II)

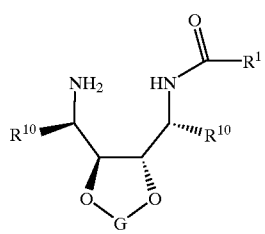

(II)

(2) contacting a compound of formula (II) with a compound of formula $R^7C(=O)H$ and subsequently contacting the imine product with a reducing agent to form a compound of formula (III):

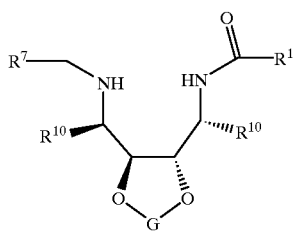

(III)

(3) contacting a compound of formula (III) with a hydrolyzing agent at a temperature sufficient to form a compound of formula (IV):

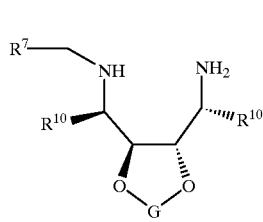

(IV)

(4) contacting a compound of formula (IV) with 3-cyano-4-fluoro-benzaldehyde and subsequently contacting the imine product with a reducing agent to form a compound of formula (V):

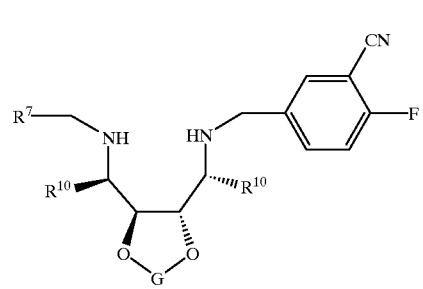

(V)

(5) contacting a compound of formula (V) with phosgene in the presence of a base to form a compound of formula (VI).

2. A process according to claim 1 wherein:

$R^7$ is $C_1$–$C_8$ alkyl or phenyl;

the reducing agent of step (2) is selected from sodium triacetoxy borohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, and $H_2$/Raney®-Nickel;

the suitable strong base in step (3) is NaOH or KOH;

the reducing agent of step (4) is selected from sodium triacetoxy borohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, and $H_2$/Raney®-Nickel; and the base in step (5) is selected from triethylamine, N,N-diisopropylethylamine, N,N-dimethyloctylamine, N,N,N',N'-tetramethylethylenediamine, tris(hydroxymethyl)aminomethane, and 1,8-bis(dimethylamino)napthalene.

3. A process according to claim 1 for the preparation of a compound of formula (VI-b):

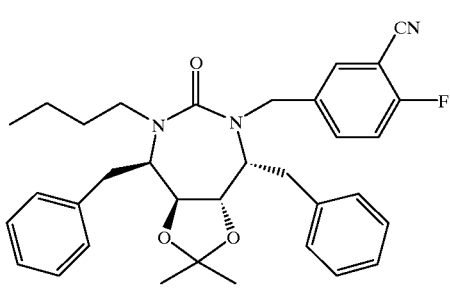
(VI-b)

said process comprising:

(1) contacting a compound of formula (I-a):

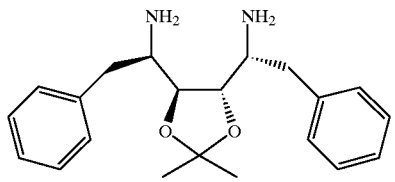
(I-a)

with an acylating agent of formula $R^1C(=O)R^2$;

wherein:

$R^1$ is $C_1$–$C_4$ haloalkyl;

$R^2$ is —$OR^3$, —$SR^3$, O-succinimide, or imidazolyl;

$R^3$ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;

$R^{3a}$ is selected from the group:
$C_1$–$C_4$ alkyl, $C_1$–$C_4$ alkoxy, halo, —CN, and —$NO_2$;

to form a compound of formula (II-a)

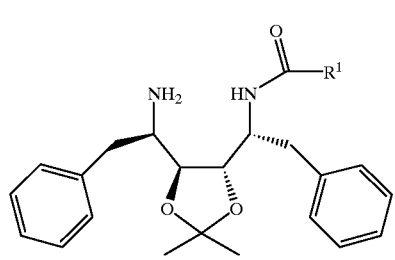
(II-a)

(2) contacting a compound of formula (II-a) with butanal and subsequently contacting the imine product with a reducing agent to form a compound of formula (III-b):

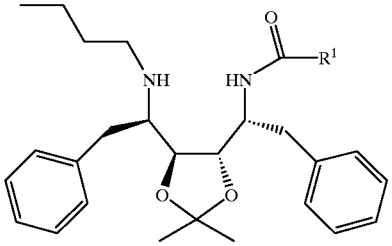
(III-b)

(3) contacting a compound of formula (III-b) with a hydrolyzing agent at a temperature sufficient to form a compound of formula (IV-b):

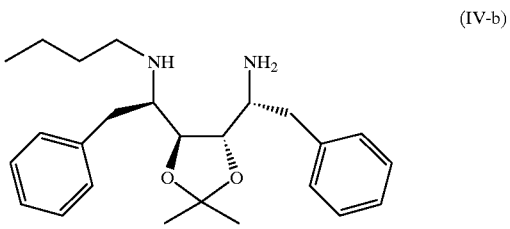
(IV-b)

(4) contacting a compound of formula (IV-b) with 3-cyano-4-fluoro-benzaldehyde and subsequently contacting the imine product with a reducing agent to form a compound of formula (V-b):

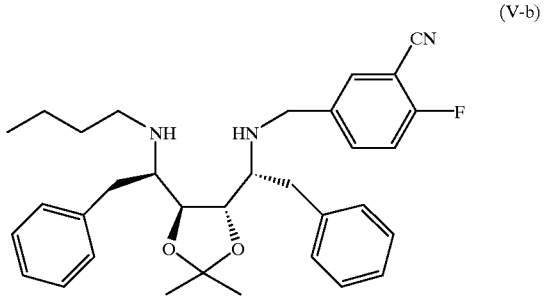
(V-b)

(5) contacting a compound of formula (V-b) with phosgene in the presence of a base to form a compound of formula (VI).

4. A process according to claim 3 wherein:
the reducing agent of step (2) is selected from sodium triacetoxy borohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, and $H_2$/Raney®-Nickel;
the in step (3) is NaOH or KOH;
the reducing agent of step (4) is selected from sodium triacetoxy borohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, and $H_2$/Raney®-Nickel; and
the base in step (5) is selected from triethylamine, N,N-diisopropylethylamine, N,N-dimethyloctylamine, N,N,N',N'-tetramethylethylenediamine, tris(hydroxymethyl)aminomethane, and 1,8-bis(dimethylamino) napthalene.

5. A process according to claim 3 wherein:
the reducing agent of step (2) is sodium triacetoxy borohydride or H₂/Pt/C;
the hydrolyzing agent in step (3) is NaOH or KOH;
the reducing agent of step (4) is sodium triacetoxy borohydride; and
the base in step (5) is tris(hydroxymethyl)aminomethane or N,N,N',N'-tetramethylethylenediamine.

6. A process according to claim 1 for the preparation of a compound of formula (VI-a):

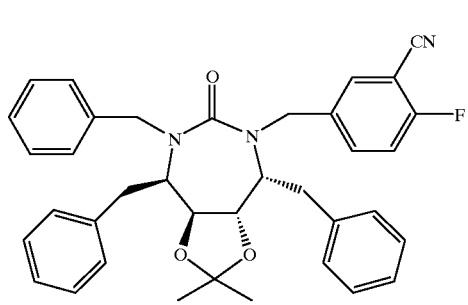

(VI-a)

said process comprising:
(1) contacting a compound of formula (I-a):

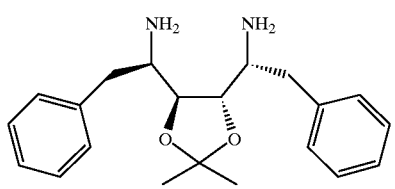

(I-a)

with an acylating agent of formula R¹C(=O)R²;
wherein:
R¹ is $C_1$–$C_4$ haloalkyl;
R² is —OR³, —SR³, O-succinimide, or imidazolyl;
R³ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;
$R^{3a}$ is selected from the group:
$C_1$–$C_4$ alkyl, $C_1$–$C_4$ alkoxy, halo, —CN, and —NO₂;
to form a compound of formula (II-a)

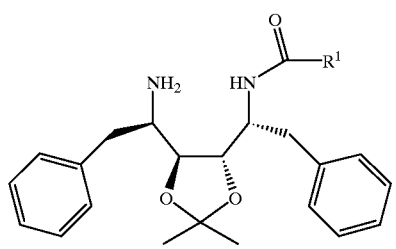

(II-a)

(2) contacting a compound of formula (II-a)) with benzaldehyde and subsequently contacting the imine product with a reducing agent to form a compound of formula (III-a):

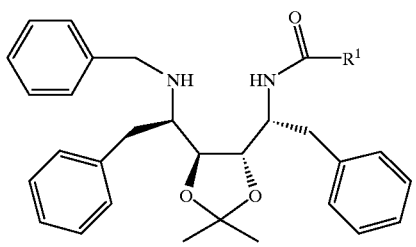

(III-a)

(3) contacting a compound of formula (III-a) with a at a temperature sufficient to form a compound of formula (IV-a):

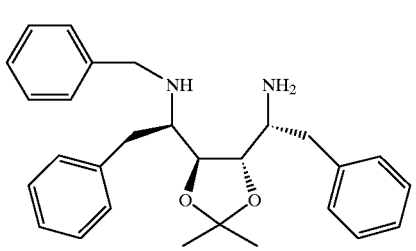

(IV-a)

(4) contacting a compound of formula (IV-a) with 3-cyano-4-fluoro-benzaldehyde and subsequently contacting the imine product with a reducing agent to form a compound of formula (V-a):

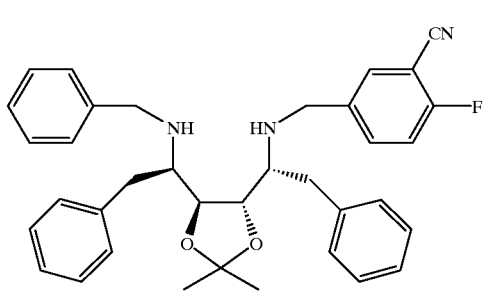

(V-a)

(5) contacting a compound of formula (V-a) with phosgene in the presence of a base to form a compound of formula (VI).

7. A process according to claim 6 wherein:
the reducing agent of step (2) is selected from sodium triacetoxy borohydride, sodium borohydride, pyridine/borane, lithium aluminium hydride, lithium borohydride, sodium cyanoborohydride, sodium amalgam, H₂/Pd/C, H₂/Pt/C, H₂/Rh/C, and H₂/Raney®-Nickel;
the in step (3) is NaOH or KOH;
the reducing agent of step (4) is selected from sodium triacetoxy borohydride, sodium borohydride, pyridine/borane, lithium aluminium hydride, lithium borohydride, sodium cyanoborohydride, sodium amalgam, H₂/Pd/C, H₂/Pt/C, H₂/Rh/C, and H₂/Raney®-Nickel; and
the suitable base in step (5) is selected from triethylamine, N,N-diisopropylethylamine, N,N-dimethyloctylamine, N,N,N',N'-tetramethylethylenediamine, tris (hydroxymethyl)aminomethane, and 1,8-bis(dimethylamino)napthalene.

8. A process according to claim 6 wherein:

the reducing agent of step (2) is sodium triacetoxy borohydride or $H_2/Pt/C$;

the in step (3) is NaOH or KOH;

the reducing agent of step (4) is sodium triacetoxy borohydride; and the base in step (5) is tris(hydroxymethyl)aminomethane or N,N,N',N'-tetramethylethylenediamine.

9. A process for the preparation of a compound of formula (II):

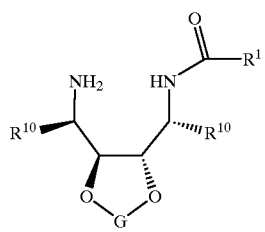

(II)

wherein:

$R^1$ is $C_1$–$C_4$ haloalkyl;

$R^{10}$ is $C_1$–$C_{10}$ alkyl, benzyl, naphthylmethyl, 3,4-methylenedioxybenzyl, or $C_1$–$C_4$ alkyl substituted with phenyl wherein said phenyl is substituted with 0–3 $R^{10a}$;

$R^{10a}$ is $C_1$–$C_4$ alkyl, $C_1$–$C_4$ alkoxy, halo or cyano; and

G taken together along with the oxygen atoms to which G is attached forms a group selected from:
—O—C(—CH$_2$CH$_2$CH$_2$CH$_2$CH$_2$—)—O—, —O—C(CH$_2$CH$_3$)$_2$—O—, —O—C (CH$_3$) (CH$_2$CH$_3$)—O—, —O—C(CH$_2$CH$_2$CH$_2$CH$_3$)$_2$—O—, —O—C(CH$_3$)(CH$_2$CH(CH$_3$)CH$_3$)—O—, —O—CH(phenyl)—O—, —OCH$_2$O—, —OC(CH$_3$)$_2$O—, and —OC(OCH$_3$) (CH$_2$CH$_2$CH$_3$)O—;

the process, comprising:

(1) contacting a compound of formula (I):

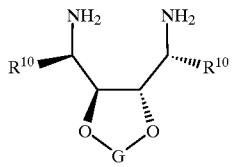

(I)

with an acylating agent of formula $R^1C(=O)R^2$;

wherein:

$R^2$ is —OR$^3$, —SR$^3$, O-succinimide, or imidazolyl;

$R^3$ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;

$R^{3a}$ is selected from the group:
$C_1$–$C_4$ alkyl, $C_1$–$C_4$ alkoxy, halo, —CN, and —NO$_2$;

to form a compound of formula (II).

10. A process according to claim 9 for the preparation of a compound of formula (II), wherein:

$R^1$ is —CF$_3$, —CF$_2$CF$_3$, —CF$_2$CF$_2$CF$_3$, —CF$_2$Cl, —CF$_2$Br, —CCl$_3$, —CBr$_3$, or CH$_2$F; and $R^2$ is —OCH$_3$ or —OCH$_2$CH$_3$.

11. A process according to claim 9 for the preparation of a compound of formula (II), wherein:

$R^1$ is —CF$_3$; and $R^2$ is —OCH$_3$, —OCH$_2$CH$_3$, —OCH$_2$CH$_2$CH$_3$, —OCH(CH$_3$)$_2$, —OCH$_2$CH=CH$_2$, —OCH$_2$CF$_3$, —SCH$_2$CH$_3$, —O-phenyl, —O—(4-nitrophenyl), or —O—(2-pyridine).

12. A process according to claim 9 for the preparation of a compound of formula (II), wherein:

$R^1$ is —CF$_3$; and $R^2$ is —OCH$_3$, —OCH$_2$CH$_3$, —SCH$_2$CH$_3$, or —O-phenyl.

13. A process according to claim 9, further comprising contacting a compound of formula (II) with a acid to form an acid addition salt.

14. A process according to claim 13, wherein the acid is selected from phthalic acid, salicylic acid, isophthalic acid, and malonic acid.

15. A process according to claim 13, wherein the acid is phthalic acid.

16. A process according to claim 9 for the preparation of a compound of formula (II):

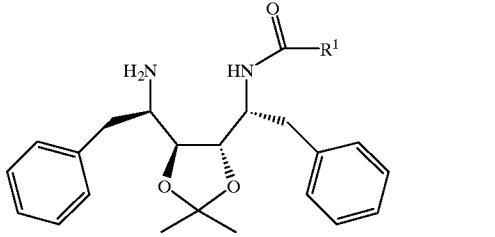

(II)

wherein $R^1$ is $C_1$–$C_4$ haloalkyl;

the process, comprising:

(1) contacting a compound of formula (I-a):

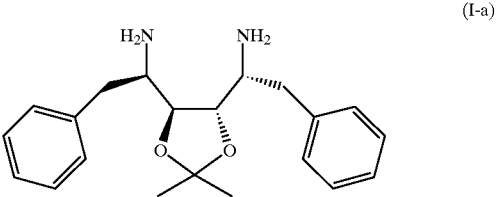

(I-a)

with an acylating agent of formula $R^1C(=O)R^2$;

wherein:

$R^2$ is —OR$^3$, —SR$^3$, O-succinimide, or imidazolyl;

$R^3$ is selected from the group:
$C_1$–$C_6$ alkyl, $C_2$–$C_6$ alkene, $C_2$–$C_6$ alkyne, $C_1$–$C_4$ haloalkyl, $C_3$–$C_{10}$ cycloalkyl, pentafluorophenyl, pyridin-2-yl, and phenyl substituted with 0–3 $R^{3a}$;

$R^{3a}$ is selected from the group:
$C_1$–$C_4$ alkyl, $C_1$–$C_4$ alkoxy, halo, —CN, and —NO$_2$;

to form a compound of formula (II).

17. A process according to claim 16 for the preparation of a compound of formula (II), wherein:

$R^1$ is —CF$_3$, —CF$_2$CF$_3$, —CF$_2$CF$_2$CF$_3$, —CF$_2$Cl, —CF$_2$Br, —CCl$_3$, —CBr$_3$, or CH$_2$F; and $R^2$ is —OCH$_3$ or —OCH$_2$CH$_3$.

18. A process according to claim 16 for the preparation of a compound of formula (II), wherein:

$R^1$ is —$CF_3$; and $R^2$ is —$OCH_3$, —$OCH_2CH_3$, —$OCH_2CH_2CH_3$, —$OCH(CH_3)_2$, —$OCH_2CH=CH_2$, —$OCH_2CF_3$, —$SCH_2CH^3$, —O-phenyl, —O—(4-nitrophenyl), or —O—(2-pyridine).

19. A process according to claim 16 for the preparation of a compound of formula (II), wherein:

$R^1$ is —$CF_3$; and $R^2$ is —$OCH_3$, —$OCH_2CH_3$, —$SCH_2CH_3$, or —O-phenyl.

20. A process for the preparation of a compound of formula (VI):

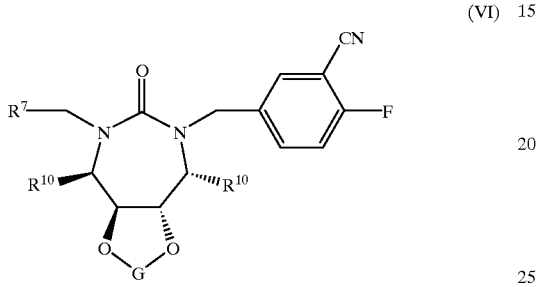

(VI)

wherein:

$R^7$ is selected from the following:
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$; and
  a $C_3$–$C_{14}$ carbocyclic ring system substituted with 0–3 $R^{11}$;

$R^{10}$ is $C_1$–$C_{10}$ alkyl, benzyl, naphthylmethyl, 3,4-methylenedioxybenzyl, or $C_1$–$C_4$ alkyl substituted with phenyl wherein said phenyl is substituted with 0–3 $R^{10a}$;

$R^{10a}$ is $C_1$–$C_4$ alkyl, $C_1$–$C_4$ alkoxy, halo or cyano;

$R^{11}$ is selected from one or more of the following:
  $C_1$–$C_4$ alkoxy, $C_1$–$C_4$ alkyl, $C_2$–$C_6$ alkoxyalkyl, benzyl, phenethyl, phenoxy, benzyloxy, methylenedioxy, ethylenedioxy, $C_2$–$C_4$ alkenyl, $C_3$–$C_{10}$ cycloalkyl, $C_3$–$C_6$ cycloalkylmethyl, $C_3$–$C_6$ cycloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy;
  —$C(=O)R^{13}$, oxo, cyano, nitro, —$CH_2NR^{13}R^{14}$, —$NR^{13}R^{14}$, —$CO_2R^{13}$, —$OC(=O)R^{13}$, —$OR^{13}$, —$OCH_2CO_2R^{13}$, —$S(O)_2R^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$;
  $C_1$–$C_4$ alkyl substituted with —$NR^{13}R^{14}$; and
  $C_3$–$C_{14}$ carbocyclic residue substituted with 0–3 $R^{16}$;

$R^{13}$ is independently selected from:
  $C_1$–$C_6$ alkyl substituted with 0–3 $R^{15}$;
  $C_2$–$C_6$ alkenyl substituted with 0–3 $R^{15}$; and
  phenyl substituted with 0–3 $R^{16}$;

$R^{14}$ is independently selected from:
  $C_1$–$C_6$ alkoxy, $C_2$–$C_6$ alkenyl, phenyl, benzyl, and $C_1$–$C_6$ alkyl substituted with 0–3 $C_1$–$C_4$ alkoxy; or $R^{13}$ and $R^{14}$ can alternatively join to form —$(CH_2)_4$—, —$(CH_2)_5$—, —$CH_2CH_2N(CH_3)CH_2CH_2$—, or —$CH_2CH_2OCH_2CH_2$—;

$R^{15}$ is selected from one or more of the following:
  $C_1$–$C_4$ alkoxy, $C_1$–$C_4$ alkyl, $C_2$–$C_6$ alkoxyalkyl, benzyl, phenethyl, phenoxy, benzyloxy, methylenedioxy, ethylenedioxy, $C_2$–$C_4$ alkenyl, $C_3$–$C_{10}$ cycloalkyl, $C_3$–$C_6$ cycloalkylmethyl, $C_3$–$C_6$ cycloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy;
  —$C(=O)R^{23}$, cyano, nitro, —$CH_2NR^{23}R^{24}$, —$NR^{23}R^{24}$, —$CO_2R^{23}$, —$OC(=O)R^{23}$, —$OR^{23}$, —$OCH_2CO_2R^{23}$, —$S(O)_2R^{23}$, —$C(=O)NR^{23}R^{24}$, —$NR^{24}C(=O)R^{23}$, =$NOR^{24}$, —$NR^{24}C(=O)OR^{24}$, —$OC(=O)NR^{23}R^{24}$, —$NR^{23}C(=O)NR^{23}R^{24}$, —$NR^{24}SO_2NR^{23}R^{24}$, —$NR^{24}SO_2R^{23}$, —$SO_2NR^{23}R^{24}$;
  $C_1$–$C_4$ alkyl substituted with —$NR^{23}R^{24}$; and
  phenyl substituted with 0–3 $R^{16}$;

$R^{16}$ is selected from one or more of the following:
  H, halogen, cyano, nitro, —$CH_2NR^{23}R^{24}$, —$NR^{23}R^{24}$, —$CO_2R^{23}$, —$OC(=O)R^{23}$, —$OR^{23}$, —$S(O)_2R^{23}$, —$C(=O)NR^{23}R^{24}$, —$NR^{24}C(=O)R^{23}$, =$NOR^{24}$, —$NR^{24}C(=O)OR^{24}$, —$OC(=O)NR^{23}R^{24}$, —$NR^{23}C(=O)NR^{23}R^{24}$, —$NR^{24}SO_2NR^{23}R^{24}$, —$NR^{24}SO_2R^{23}$, —$SO_2NR^{23}R^{24}$;
  $C_1$–$C_4$ alkyl, $C_2$–$C_4$ alkenyl, $C_3$–$C_6$ cycloalkylmethyl, phenyl, benzyl, phenethyl, phenoxy, benzyloxy, $C_3$–$C_6$ cycloalkoxy, methylenedioxy, ethylenedioxy, $C_1$–$C_4$ alkoxycarbonyl, pyridylcarbonyloxy, $C_1$–$C_4$ alkylcarbonyl, $C_1$–$C_4$ alkylcarbonylamino, 2-(1-morpholino)ethoxy; and
  $C_1$–$C_4$ alkyl substituted with —$NR^{23}R^{24}$;

$R^{23}$ is $C_1$–$C_4$ alkyl substituted with 0–3 $C_1$–$C_4$ alkoxy;

$R^{24}$ is $C_1$–$C_4$ alkyl substituted with 0–3 $C_1$–$C_4$ alkoxy; or $R^{23}$ and $R^{24}$ can alternatively join to form —$(CH_2)_4$—, —$(CH_2)_5$—, —$CH_2CH_2N(CH_3)CH_2CH_2$—, or —$CH_2CH_2OCH_2CH_2$—; and G taken together along with the oxygen atoms to which G is attached forms a group selected from:
  —O—C(—$CH_2CH_2CH_2CH_2CH_2$—)—O—, —O—C$(CH_2CH_3)_2$—O—, —O—C$(CH_3)$ $(CH_2CH_3)$—O—, —O—C$(CH_2CH_2CH_2CH_3)_2$—O—, —O—C$(CH_3)$ $(CH_2CH(CH_3)CH_3)$—O—, —O—CH(phenyl)—O—, —$OCH_2O$—, —$OC(CH_3)_2O$—, and —$OC(OCH_3)$ $(CH_2CH_2CH_3)O$—;

said process comprising:

(5) contacting a compound of formula (V):

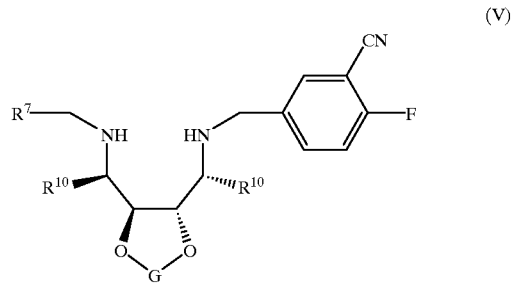

(V)

with a cyclizing agent selected from phosgene, diphosgene, and triphosgene, in the presence of a base to form a compound of formula (VI).

21. A process according to claim 20 wherein the base in step (5) is selected from triethylamine, N,N-diisopropylethylamine, N,N-dimethyloctylamine, N,N,N',N'-tetramethylethylenediamine, tris(hydroxymethyl)aminomethane, and 1,8-bis(dimethylamino)napthalene.

22. A process according to claim 20 for the preparation of a compound of formula (VI):

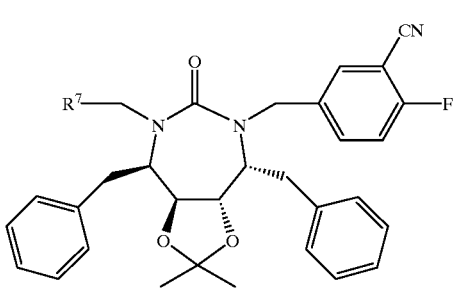

wherein:

R⁷ is $C_1$–$C_8$ alkyl or phenyl;

said process comprising:

(5) contacting a compound of formula (V):

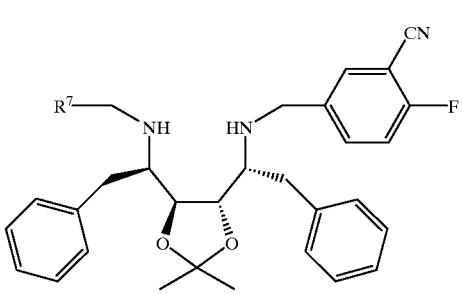

with a cyclizing agent selected from phosgene, diphosgene, and triphosgene, in the presence of a base to form a compound of formula (VI).

23. A process according to claim 22 wherein the base in step (5) is selected from triethylamine, N,N-diisopropylethylamine, N,N-dimethyloctylamine, N,N,N', N'-tetramethylethylenediamine, tris(hydroxymethyl) aminomethane, and 1,8-bis(dimethylamino)napthalene.

24. A process according to claim 20 for the preparation of a compound of formula (VI):

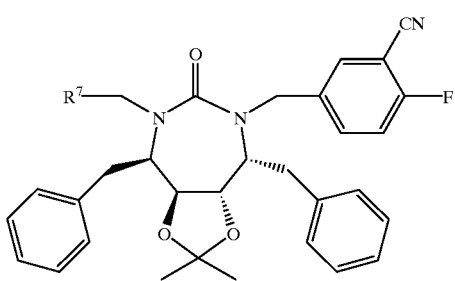

wherein R⁷ is propyl or phenyl;

said process comprising:

(5) contacting a compound of formula (V):

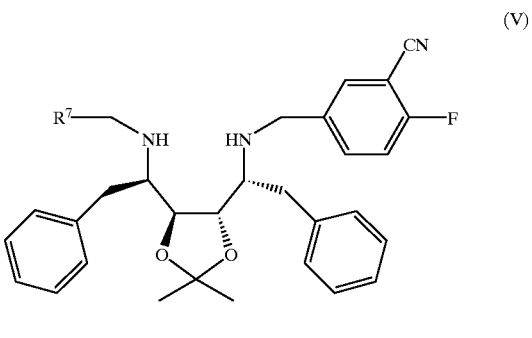

with phosgene in the presence of a base to form a compound of formula (VI).

25. A process according to claim 24 wherein the base in step (5) is selected from triethylamine, N,N-diisopropylethylamine, N,N-dimethyloctylamine, N,N,N', N'-tetramethylethylenediamine, tris(hydroxymethyl) aminomethane, and 1,8-bis dimethylamino)napthalene.

26. A process according to claim 24 wherein the base in step (5) is tris(hydroxymethyl)aminomethane or N,N,N',N'-tetramethylethylenediamine.

27. A process according to claim 1 further comprising:

(6) contacting a compound of formula (VI) with hydrazine, or a hydrazine equivalent selected from the group consisting of anhydrous hydrazine, hydrazine hydrate, and salts of hydrazine, under conditions sufficient to form a compound of formula (X):

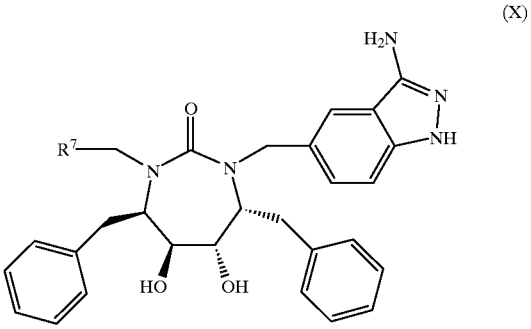

or a pharmaceutically acceptable salt form thereof; wherein a condition sufficient to form a compound of formula (X) comprises:

(a) removing the diol protecting group G of formula (VI) before contacting a compound of formula (VI) with hydrazine, or a hydrazine equivalent; or (b) removing the diol protecting group G of formula (VI) after contacting a compound of formula (VI) with hydrazine, or a hydrazine equivalent.

28. A process according to claim 20 further comprising:

(6) contacting a compound of a (VI) with hydrazine, or a hydrazine equivalent selected from the group consisting of anhydrous hydrazine, hydrazine hydrate, and salts of hydrazine, under conditions sufficient to form a compound of formula (X):

(X) 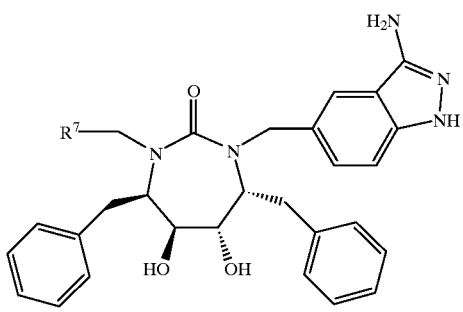

or a pharmaceutically acceptable salt form thereof; wherein a condition sufficient to form a compound of formula (X) comprises:

(a) removing the diol protecting group G of formula (VI) before contacting a compound of formula (VI) with hydrazine, or a hydrazine equivalent; or (b) removing the diol protecting group G of formula (VI) after contacting a compound of formula (VI) with hydrazine, or a hydrazine equivalent.

* * * * *